United States Patent
Chen et al.

(10) Patent No.: US 9,389,167 B2
(45) Date of Patent: Jul. 12, 2016

(54) MULTICHANNEL ANALYTICAL INSTRUMENTS FOR USE WITH SPECIMEN HOLDERS

(71) Applicant: Laxco, Inc., Bothell, WA (US)

(72) Inventors: Cong Liang Chen, Woodinville, WA (US); Kevin Cassady, Monroe, WA (US)

(73) Assignee: LAXCO, INC., Bothell, WA (US)

(*) Notice: Subject to any disclaimer, the term of this patent is extended or adjusted under 35 U.S.C. 154(b) by 0 days.

(21) Appl. No.: 14/873,036

(22) Filed: Oct. 1, 2015

(65) Prior Publication Data

US 2016/0025616 A1  Jan. 28, 2016

Related U.S. Application Data

(63) Continuation of application No. 13/782,950, filed on Mar. 1, 2013, now Pat. No. 9,182,336.

(60) Provisional application No. 61/606,214, filed on Mar. 2, 2012.

(51) Int. Cl.
*G01N 21/01* (2006.01)
*G01N 21/03* (2006.01)
(Continued)

(52) U.S. Cl.
CPC ............ *G01N 21/0303* (2013.01); *G01N 21/01* (2013.01); *G01N 21/17* (2013.01);
(Continued)

(58) Field of Classification Search
CPC ........... G01N 21/01; G01N 27/17; G02B 6/04
USPC ................... 250/221, 227.11, 227.24, 227.25, 250/227.28; 356/246, 326, 432, 440; 385/31
See application file for complete search history.

(56) References Cited

U.S. PATENT DOCUMENTS

| | | | |
|---|---|---|---|
| 4,286,881 | A | 9/1981 | Janzen |
| 4,643,580 | A | 2/1987 | Gross et al. |

(Continued)

FOREIGN PATENT DOCUMENTS

| | | |
|---|---|---|
| DE | 198 24 652 A1 | 1/2000 |
| EP | 0 062 160 A1 | 10/1982 |

(Continued)

OTHER PUBLICATIONS

Chen et al., "Multichannel Analytical Instruments for Use With Specimen Holders," Amendment filed Jul. 21, 2015, for U.S. Appl. No. 13/782,950, 11 pages.

(Continued)

*Primary Examiner* — Kevin Pyo
(74) *Attorney, Agent, or Firm* — Seed IP Law Group PLLC

(57) ABSTRACT

An analytical instrument may have multiple distinct channels. Such may include one or more illumination sources and sensors. Illumination may be delivered to specific locations of a specimen holder, and returned illumination may be delivered to specific locations of a sensor array. Illumination may first pass a specimen, and a mirror or reflector may then return the illumination past the specimen. Optical splitters may be employed to couple pairs of fiber optics proximate a specimen holder. Such channels may further include a plurality of illumination sources positioned on one side of a specimen holder and a plurality of sensors on the other side. The plurality of sensor may capture image of a specimen and a spectrophotometer may concurrently scan the specimen. A plurality of specimens may be imaged and scanned in a single pass of a plurality of passes. Spherical or ball lenses may be placed in an optical path of the illumination to achieve a desired illumination pattern.

26 Claims, 27 Drawing Sheets

(51) Int. Cl.
*G01N 21/17* (2006.01)
*G02B 6/04* (2006.01)
*G01N 21/25* (2006.01)
*G01N 21/27* (2006.01)
*G02B 6/32* (2006.01)
*F21V 8/00* (2006.01)
*G02B 6/293* (2006.01)
*G01N 21/64* (2006.01)

(52) U.S. Cl.
CPC ............ *G01N 21/253* (2013.01); *G01N 21/27* (2013.01); *G02B 6/04* (2013.01); *G01N 21/6452* (2013.01); *G01N 2201/0639* (2013.01); *G01N 2201/08* (2013.01); *G01N 2201/0826* (2013.01); *G02B 6/006* (2013.01); *G02B 6/29388* (2013.01); *G02B 6/32* (2013.01)

(56) References Cited

U.S. PATENT DOCUMENTS

| | | | |
|---|---|---|---|
| 4,910,402 A | | 3/1990 | McMillan |
| 4,950,077 A | | 8/1990 | Manabe |
| 5,450,194 A | * | 9/1995 | Dureault ............ G02B 6/2848 356/319 |
| 5,739,432 A | | 4/1998 | Sinha |
| 6,628,382 B2 | | 9/2003 | Robertson |
| 6,661,512 B2 | | 12/2003 | Fernando et al. |
| 6,809,826 B2 | | 10/2004 | Robertson |
| 7,414,724 B2 | | 8/2008 | Eckert et al. |
| 7,483,138 B2 | | 1/2009 | Sahiri et al. |
| 7,688,429 B2 | | 3/2010 | Sahari et al. |
| 7,872,749 B2 | | 1/2011 | Robertson et al. |
| 7,928,408 B2 | | 4/2011 | Ok et al. |
| 9,255,844 B2 | * | 2/2016 | Juuti .................... G01J 3/51 |
| 2002/0113213 A1 | * | 8/2002 | Amirkhanian ... G01N 27/44782 250/458.1 |
| 2007/0139639 A1 | | 6/2007 | Tsien et al. |
| 2008/0106742 A1 | | 5/2008 | Sahiri et al. |
| 2008/0204755 A1 | | 8/2008 | Sahiri et al. |

FOREIGN PATENT DOCUMENTS

| | | |
|---|---|---|
| EP | 0 973 040 A2 | 1/2000 |
| WO | 01/14855 A1 | 3/2001 |
| WO | 2010/123883 A2 | 10/2010 |
| WO | 2011/139641 A2 | 11/2011 |

OTHER PUBLICATIONS

Chen et al., "Multichannel Analytical Instruments for Use With Specimen Holders," Office Action mailed Jun. 3, 2015 for U.S. Appl. No. 13/782,950, 10 pages.

Extended European Search Report dated Oct. 6, 2015, for corresponding EP Application No. 13754510.9-1554, 12 pages.

International Search Report, mailed Jun. 21, 2013, for PCT/US2013/028693, 3 pages.

Thermo Scientific, NanoDrop 1000 Spectrophotometer—V3.7 User's Manual, revised Jul. 2008, 105 pages.

Written Opinion, mailed Jun. 21, 2013, for PCT/US2013/028693, 4 pages.

\* cited by examiner

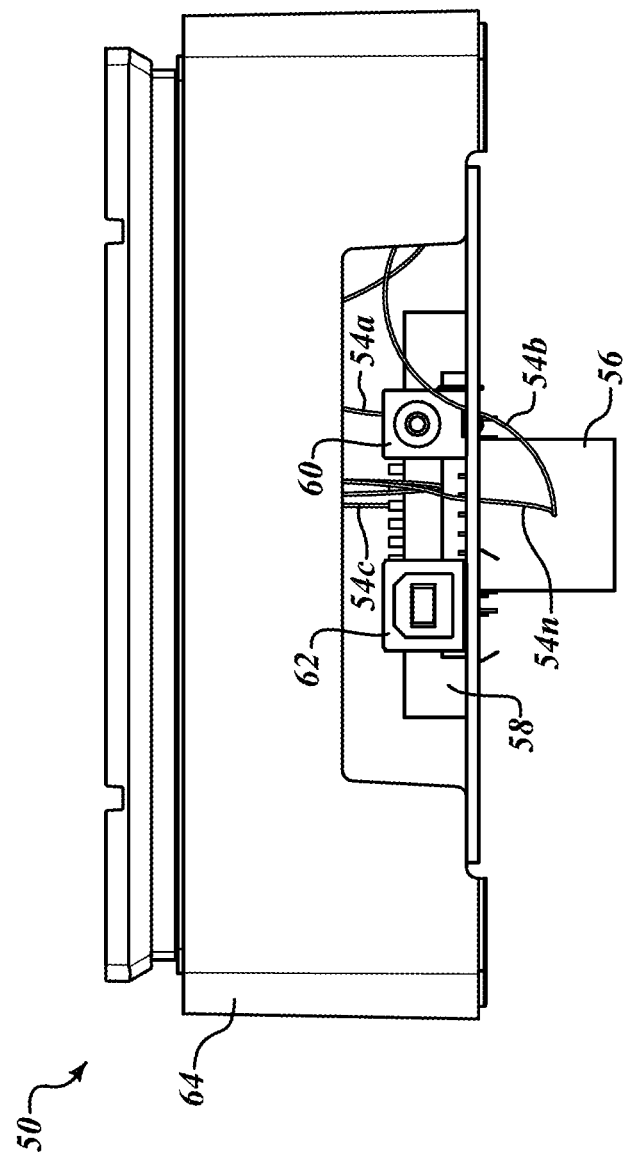

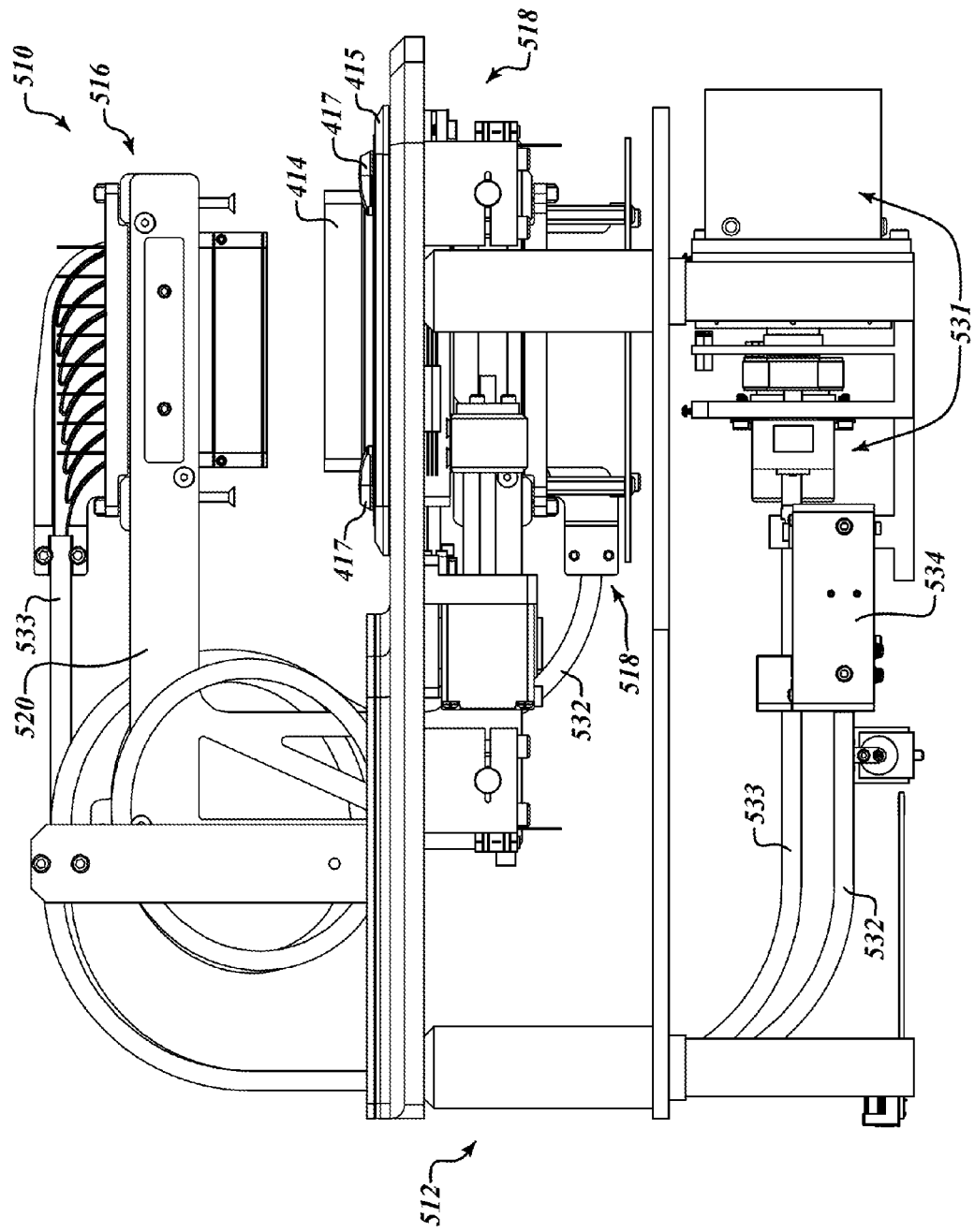

MULTICHANNEL ANALYTICAL INSTRUMENTS FOR USE WITH SPECIMEN HOLDERS

BACKGROUND

1. Field

This disclosure generally relates to analytical instruments, and particularly analytical instruments for use with specimen holders that hold specimens or samples to be analyzed.

2. Description of the Related Art

There are numerous types of analytical instruments used for a variety of purposes, for example research, testing, and diagnostics. For example, some analytical instruments are used to detect biological substances, for instance proteins or DNA.

Many analytical instruments expose a specimen or sample of a material to be analyzed to electromagnetic energy and senses or otherwise detects a response of the specimen or sample to the exposure. For example, a specimen or sample may be exposed to illumination in one or more wavelengths or ranges of wavelengths of the electromagnetic spectrum. For instance, a specimen or sample may be exposed to or illuminated with electromagnetic energy in an optical portion of the electromagnetic spectrum, extending from infrared to ultraviolet and encompassing visible light as well as invisible light such as near infrared or near ultraviolet wavelengths. Many materials will reflect some wavelengths while absorbing other wavelengths. Some materials may reemit electromagnetic energy at a different or shifted wavelength in a phenomenon commonly referred to as fluorescence. This spectral response may be used to characterize the material.

Analytical instruments are often used with disposable specimen or sample holders which hold specimens or samples of the material to be analyzed. Specimen or sample holders may take the form of simple cuvettes or may be relatively more complicated microfluidic platforms with channels, wells, reservoirs, pumps, valves, etc. Such may come in a variety of shapes, typically plates with either a rectangular or circular profile. The specimen or sample holders are removably located in the analytical instrument.

In some instances, the specimen or sample holders also hold one or more reagents that are targeted to react with certain substances. Some reagents may for example fluoresce, aiding in identification of substances with which the reagents react.

The ability to accurately measure responses from specimens or samples is important. Achieving consistent illumination or excitation is important to producing accurate results. Such may be difficult due to alignment errors, particularly where the specimen or sample holder is removable. Typically high density of specimens or samples on a sample holder is desirable. However, closeness of specimens or samples may complicate analysis. Interference between sampling of neighboring areas or locations may also contribute to error or inaccuracies.

New approaches which may lead to improved accuracy in analytical instruments are desirable.

BRIEF SUMMARY

The analytical instruments described herein employ a configuration that may inherently provide a number of distinct advantages, some of which are discussed herein.

The configuration generally provides a number of apertures on a first side of a specimen holder which align or are in registration with respective locations of specimen holders. The locations may, for example take the form of specimen holding regions, for instance wells, reservoirs or areas that have been texturally treated, coated, or otherwise are locations at which specimens or samples are to be analyzed. This configuration allows the apertures to both direct electromagnetic energy (e.g., light) toward the respective locations of the specimen holders and to receive electromagnetic energy returned from the respective locations of the specimen holders. Thus, this configuration advantageously is inherently self-aligned. Electromagnetic energy enters and exits the specimen or sample holder from the same side or port, eliminating any need to align the sensor with the light source. Alignment is normally difficult to do since the sensor is typically positioned on the far side of the specimen or sample holder from the light source, and since the specimen or sample holder is typically removable from the analytic instrument. In fact, the specimen or sample holders are typically low-cost single-use or consumable items, and thus tend not to have high manufacturing tolerances.

This configuration also employs optical conduits, for example optical fibers to provide optical paths between the lens holder and alignment frame and both a source of electromagnetic radiation and a sensor or detector. Pairs of optical fibers, one extending from the source and the other extending to the sensor, are optically coupled via a splitter. The splitter allows both outgoing and incoming electromagnetic energy to share a portion of an optical path.

The configuration may also employ a lens holder and alignment frame. The lens holder and alignment frame advantageously aligns or registers the apertures with the locations on the specimen or sample holder. The lens holder and alignment frame may also securely position a respective lens in a respective optical path for each of the apertures or locations. The lenses may advantageously take the form of spherical or ball lenses to achieve desirable illumination or throw pattern.

The configuration may also locate a mirror or reflector on the other side of specimen holder from the apertures. The design also advantageously exposes the specimen to two passes of the illumination. In particular, a mirror or other reflector is positioned on the far side of the specimen or sample holder from the location where light enters and exits. Light that bypasses the specimen is reflected back past the specimen toward the location. This also permits a single respective lens to be used for both illuminating and collecting light from each location of the specimen or sample holder.

The configurations also permit samples to be concurrently taken from multiple locations across a specimen holder. Such may greatly increase throughput over serial sampling.

The configurations may also advantageously provide a particularly compact design. Such may increase portability, reduce power requirements. The compact design may even allow the analytical instrument to be used in locations or situations where other less compact analytical instruments could not be used. For example, the compact design may allow the analytical instrument to be placed in incubators.

A multi-channel analytical instrument may be summarized as including: at least one illumination source operable to emit electromagnetic energy; a receiver having at least a first portion and a second portion, the second portion opposed to the first portion, at least the first and the second portions positioned with respect to one another to form at least one receptacle therebetween which is sized and shaped to at least partially receive at least one specimen or sample holder, the first portion of the receiver permits the passage of electromagnetic energy emitted by the at least one illumination source into the receptacle and the second portion of the receiver substantially reflects electromagnetic energy emitted by the at least one illumination source back into the receptacle; and at least one sensor responsive to electromagnetic energy returned from the at least one receptacle to produce a signal indicative of at least one characteristic thereof.

The second portion may be a mirror. The mirror may reflect at least ultraviolet wavelengths of electromagnetic energy. The second portion may be a mirror plate and the first portion may be a plate that is substantially transparent to at least some wavelengths of the electromagnetic energy emitted by the at least one illumination source. The multi-channel analytical instrument may further include: a number of illumination conduits that couple electromagnetic energy between the at least one illumination source and at least the receiver. 6. The number of illumination conduits may include at least 8 optical fibers. The multi-channel analytical instrument may further include: a number of sampling conduits that couple electromagnetic energy between the receiver and the at least one sensor. The number of sampling conduits may include at least 8 optical fibers. The multi-channel analytical instrument may further include: a plurality of ball lenses each positioned at a respective one of a plurality of positions spaced from one another along a dimension of the receptacle and in an optical path between the receptacle and at least one of the at least one illumination source or the at least one sensor. The multi-channel analytical instrument may further include: a first number of optical fibers that couple electromagnetic energy between the at least one illumination source and at least the receiver; and a second number of optical fibers that couple electromagnetic energy between the receiver and the at least one sensor, wherein each of the optical fibers of the second number of optical fibers is coupled to a respective one of optical fibers of the first number of optical fibers via a respective splitter. The multi-channel analytical instrument may further include: a plurality of ball lenses each positioned at a respective one of a plurality of positions spaced from one another along a dimension of the receptacle and in an optical path between the receptacle and at least one of the first number of optical fibers at or the second number of optical fibers. The at least one illumination source may include a plurality of individual light sources, each operable to emit electromagnetic energy in respective bands of wavelengths, at least one of the bands of wavelengths different from at least another one of the bands of wavelengths. The receiver may removably receive a single specimen or sample holder in the receptacle in the form of a multi-well specimen or sample holder having wells spaced along a first dimension thereof. The receiver removably may receive a plurality of specimen or sample holders in the receptacle in the form of individual cuvettes.

A multi-channel analytical instrument may be summarized as including: at least one illumination source operable to emit electromagnetic energy; a receiver that has at least one receptacle to at least partially receive at least one specimen or sample holder, the receptacle having at least a first dimension along which samples are spaced in use; at least one sensor responsive to electromagnetic energy returned from the at least one receptacle to produce a signal indicative of at least one characteristic of the returned electromagnetic energy; a plurality of optical fibers coupled between the receiver and at least one of the at least one illumination source or the at least one sensor; and a plurality of ball lenses each positioned at a respective one of a plurality of positions spaced from one another along the first dimension of the receptacle and in an optical path between a respective at least one of the optical fibers and the receptacle.

Each of the ball lenses may be in an optical path between the receptacle and both of a respective first optical fiber and a respective second optical fiber, the respective first optical fiber coupled to the at least one illumination source and the respective second optical fiber coupled to the at least one sensor. The receiver may be an assembly that includes a coupler having a plurality of passages in which respective ones of the ball lenses are received and to which the respective first and the respective second optical fibers are coupled. 18. The multi-channel analytical instrument of claim 17 wherein the assembly may include a passage portion that permits the passage of electromagnetic energy emitted by the at least one illumination source and a reflection portion that substantially reflects electromagnetic energy emitted by the at least one illumination source back toward the receptacle. The passage portion of the assembly may be a plate that is substantially transparent to at least some wavelengths of electromagnetic energy emitted by the at least one light source and the reflection portion of the assembly is at least one reflector. The multi-channel analytical instrument may further include: a plurality of splitters that couple respective ones of a proximate end of the respective first optical fiber and a proximate end of the respective second optical fiber. Each of the splitters may include a fused junction between the proximate ends of the respective first and the respective second optical fibers. Each of the ball lenses may achieve an illumination pattern of approximately 2 millimeters in diameter.

A multi-channel analytical instrument may be summarized as including: at least one illumination source operable to emit electromagnetic energy; a receiver that has at least one receptacle to at least partially receive at least one specimen or sample holder; at least one sensor responsive to electromagnetic energy returned from the at least one receptacle to produce a signal indicative of at least one characteristic of the returned electromagnetic energy; a first number of optical fibers coupled between the at least one illumination source and the receiver to guide the electromagnetic energy emitted by the at least one illumination source toward the receiver; a second number of optical fibers coupled between the at least one sensor and the receiver to guide electromagnetic energy from the receptacle to the at least one sensor, and a plurality of splitters that optically couple at least some of the second number of optical fibers with a respective one of the first number of optical fibers.

Each of the splitters may include a fused junction between the proximate ends of the respective first and the respective second optical fibers. Each of the splitters may be an approximately 50:50 splitter which splits electromagnetic energy of at least some wavelengths approximately equally. The splitters may be spaced from one another along a first dimension of the receiver. The receiver may removably receive a single specimen or sample holder in the receptacle in the form of a multi-well specimen or sample holder having wells spaced along a first dimension thereof, the first dimension of the multi-well specimen or sample holder parallel with the first dimension of the receiver in use. The receiver may removably receive a plurality of specimen or sample holders in the receptacle in the form of individual cuvettes, the cuvettes received by the receiver spaced from one another along the first dimension of the receiver in use. The multi-channel analytical instrument may include at least 8 splitters. The multi-channel analytical instrument may include at least 16 splitters. The multi-channel analytical instrument may further include: a plurality of ball lenses, each of the ball lenses in an optical path between the receptacle and a respective one of the splitters. The receiver may include a first portion that permits the passage of electromagnetic energy emitted by the at least one illumination source and a second portion that substantially reflects electromagnetic energy emitted by the at least one illumination source back toward the receptacle, the splitters coupled to the first portion via respective ones of the ball lenses.

A multi-channel analytical instrument may be summarized as including: at least one illumination source operable to emit electromagnetic energy; a receiver that has at least one receptacle to at least partially receive at least one specimen or sample holder, the receiver having at least a first dimension along which samples held by the at least one specimen or sample holder are spaced in use; a first number of optical fibers each having a proximate end and a distal end, the proximate ends of the first number of optical fibers positioned to receive electromagnetic energy from a respective one of a plurality of positions spaced from one another along the first dimension of the receiver, and a linear sensor array having a linear dimension and responsive to electromagnetic energy returned from the at least one receptacle to produce a signal indicative of at least one characteristic of the returned electromagnetic energy, the distal ends of the first number of optical fibers positioned relative to the linear sensor to provide electromagnetic energy to respective positions spaced from one another along the linear dimension of the linear sensor array.

The linear sensor array may be a global shutter sensor responsive to a control signal to concurrently sample pixels across the entire linear dimension of the linear sensor. The receiver may include a coupler having a plurality of passages to which respective ones of the first number of optical fibers are optically coupled, the passages spaced along the first dimension of the receiver from one another. The multi-channel analytical instrument may further include: a plurality of ball lenses, each of the ball lenses received in a respective one of the passages of the coupler to optically couple the respective one of the first number of optical fibers to the receptacle. The first number of optical fibers may include a plurality of illumination optical fibers, the distal ends of which are optically coupled to the at least one light source, and the first number of optical fibers includes a plurality of sampling optical fibers, the distal ends of which are optically coupled to the at least one sensor, the ball lenses positioned between receptacles and the optical fibers of the first number of optical fibers. The multi-channel analytical instrument may further include: a plurality of splitters that couple respective pairs of the illumination and sampling optical fibers. Each of the splitters may include a fused junction between the respective pair of the illumination and the sampling optical fibers. The passages may be spaced along the first dimension of the receiver from one another to match a spacing of a plurality of sample receiving wells of the at least one specimen or sample holder in use. The passages may be spaced along the first dimension of the receiver from one another to match a spacing of a plurality of cuvettes received by the receiver in use. The receiver may include a first portion that permits the passage of electromagnetic energy emitted by the at least one illumination source and a second portion that substantially reflects electromagnetic energy emitted by the at least one illumination source back toward the receptacle.

A multi-channel analytical instrument may be summarized as including: sample holding means for holding a sample; illumination means for emitting illumination; sensor means for sensing at least one characteristic of illumination returned from the sample holding means concurrently at a plurality of spaced locations along a linear dimension; illumination guiding means for guiding emitted illumination from the illumination means toward the sample holding means; sampling guiding means for guiding illumination from the sample holding means toward the sensor means; reflection means for reflecting illumination in the sample holding means; splitter means for splitting illumination between the illumination guiding means and the sampling guiding means; and lenses means for increasing an area of illumination, the lenses means in an optical path between the splitter means and the sample holding means.

A multi-channel analytical instrument may be summarized as including a receiver that has at least one well to at least partially receive at least one specimen holder, the receiver having at least one first dimension along which samples are spaced in use; at least one illumination source positioned disposed on a first side of the at least one well and operable to emit electromagnetic energy through the at least one well; at least one sensor positioned disposed on a second side of the at least one well, the at least one sensor responsive to electromagnetic energy received from the at least one well to produce a signal indicative of at least one characteristic of the electromagnetic energy; a first optical fiber coupled to the at least one illumination source; a second optical fiber coupled to the at least one sensor; a plurality of first ball lenses each positioned proximate a respective one of a plurality of positions disposed on the first side of the at least one well and spaced from one another along the first dimension of the receiver; a plurality of second ball lenses each positioned proximate a respective one of a plurality of positions disposed on the second side of the at least one well and spaced from one another along the first dimension of the receiver; and at least one of the plurality of first ball lenses and at least one of the plurality of second ball lenses in an optical path between respective pairs of the first and the second optical fibers, and at least one of the at least one well in the optical path arranged therebetween along the optical path.

The multi-channel analytical instrument may further include a carriage having an illumination source mount and an illumination sensor mount, the illumination source mount supporting the first optical fiber and the plurality of first ball lenses, the illumination sensor mount supporting the second optical fiber and the plurality of second ball lenses.

The carriage may be slidably coupled to a guide member, whereby the carriage is movable in at least one direction relative to the receiver such that the at least one illumination source and the at least one sensor are movable along a plurality of wells of the receiver. The at least one well may include a passage portion that permits the passage of electromagnetic energy emitted by the at least one illumination source. Each of the ball lenses may achieve an illumination pattern of approximately 2 millimeters in diameter.

The multi-channel analytical instrument may further include a linear sensor array having a linear dimension and responsive to electromagnetic energy passed through the at least one well to produce a signal indicative of at least one characteristic of the passed-through electromagnetic energy.

The linear sensor array may be a global shutter sensor responsive to a control signal to concurrently sample pixels across the entire linear dimension of the linear sensor. The receiver may have a plurality of wells to at least partially receive a plurality of respective specimen holders, the receiver having a plurality of first dimensions along which samples are spaced in use, the plurality of first dimensions forming a multi-linear dimension throughout which samples are spaced in use.

A multi-channel analytical instrument may be summarized as including at least one illumination source operable to emit electromagnetic energy; a receiver that has at least one well to at least partially receive at least one specimen holder, the receiver having at least a first dimension along which samples held by the at least one specimen holder are spaced in use; a first number of optical fibers coupled to the at least one illumination source; a second number of optical fibers each having a proximate end and a distal end, the proximate ends of the second number of optical fibers positioned to receive electromagnetic energy from a respective one of the first number of optical fibers, the second number of optical fibers arranged along a plurality of positions spaced from one another along the first dimension of the receiver; and a linear sensor array coupled to the distal ends of the second number of optical fibers and having a linear dimension, the linear sensor array responsive to electromagnetic energy received from the first number of optical fibers by the second number of optical fibers to produce a signal indicative of at least one characteristic of the electromagnetic energy, the distal ends of the second number of optical fibers positioned relative to the linear sensor to receive electromagnetic energy provided by the first number of optical fibers spaced from one another along the linear dimension of the linear sensor array.

The linear sensor array may be a global shutter sensor responsive to a control signal to concurrently sample pixels across the entire linear dimension of the linear sensor.

The multi-channel analytical instrument may further include a plurality of first ball lenses each positioned at a respective one of a plurality of positions disposed on a first side of the at least one well and spaced from one another along the first dimension of the receiver.

The multi-channel analytical instrument may further include a plurality of second ball lenses each positioned at a respective one of a plurality of positions disposed on a second side of the at least one well and spaced from one another along the first dimension of the receiver, and at least one of the plurality of first ball lenses and at least one of the plurality of second ball lenses in an optical path between a respective first and second optical fibers, and at least one of the at least one well in the optical path positioned between the at least one of the plurality of first ball lenses and the at least one of the plurality of second ball lenses.

The receiver may include a plurality of passages that permit the passage of electromagnetic energy emitted by the at least one illumination source. The passages may be spaced along the first dimension of the receiver from one another to match a spacing of a plurality of sample receiving wells of the at least one specimen holder in use.

The multi-channel analytical instrument may further include a carriage having an illumination source mount and an illumination sensor mount, the illumination source mount supporting a distal end of the first optical fiber and the plurality of first ball lenses, the illumination sensor mount supporting a distal end of the second optical fiber and the plurality of second ball lenses.

The carriage may be slidably coupled to a guide member, whereby the carriage is movable in at least one direction relative to the receiver such that the at least one illumination source and the at least one sensor are movable along a plurality of wells of the receiver.

The multi-channel analytical instrument may further include at least eight optical fibers for the first number of optical fibers and at least eight optical fibers for the second number of optical fibers. Each set of at least eight optical fibers is movable along an axis relative to receiver. Thus, the multi-channel analytical instrument is capable of imaging a plurality of wells with 8 imaging channels at the same time. The multi-channel analytical instrument can analyze a total of 96 wells in a single specimen receiver in a single operation where the sets of optical fibers stop a total of 12 times across the specimen receiver having an 8×12 well, for example.

The multi-channel analytical instrument may further include a light source module having a filter selection apparatus with at least one filter. The light source module may be used to emit a light source through only one optical fiber at a time, which is particularly advantageous because some spectrophotometers (the sensor reading the light after transmitting through a specimen) operate better when only a single, controlled light source is emitted at a time. The light source module may include a housing having an illumination source and a channel selection apparatus. The housing is configured to a couple a fiber bundle of a plurality of optical fibers. The illumination source is operable to emit electromagnetic energy in an energy path. The channel selection apparatus includes an opening positioned in the energy path between the illumination source and the first plurality of optical fibers. The channel selection apparatus is configured to position any single one of the plurality of optical fibers in the energy path. The light source module may have a filter selection apparatus having at least one filter positionable in the energy path. The filter selection apparatus may include a pair of filters positionable in the energy path between the illumination source and the plurality of optical fibers.

Thus, the channel selection apparatus can choose a particular optical fiber and the filter selection apparatus can choose a particular filter for illumination of light therethrough from the at least one light source to the selected fiber, and therefore through a particular specimen. This process can be repeated such that any number of filters and light sources could be used for any number of selected optical fibers. In some embodiments, the light source module includes a first lens and a second lens. The first lens is positioned between the at least one filter and the at least one illumination source, and the second lens positioned between the at least one filter and the selected single optical fiber. The light source module controls light intensity transmitted through a particular specimen, which is advantageous because different specimens respond to different wavelengths.

A multi-channel analytical instrument may be summarized as including sample holding means for holding a sample; illumination means for emitting illumination; sensor means for sensing at least one characteristic of illumination received from the illumination means concurrently at a plurality of spaced locations along a linear dimension; illumination guiding means for guiding emitted illumination from the illumination means toward the sample holding means; sampling guiding means for guiding illumination from the sample holding means toward the sensor means; first lenses means for increasing an area of illumination; and second lenses means for receiving the area of illumination, the sample holding means in an optical path between the first lenses means and the second lenses means.

The multi-channel analytical instrument may further include traversing means for moving the first lenses means and the second lenses means relative to the sample holding means.

The multi-channel analytical instrument may further include filter selection means for selecting at least one filter to position in an optical path with the illumination means. The multi-channel analytical instrument may further include channel selection means for selecting a single optical fiber of a plurality of fibers of the illumination means and positioning means for positioning the single optical fiber in the optical path.

A multi-channel analytical instrument may be summarized as including: a sample holding means for holding a plurality of samples; a first illumination means for emitting illumination; a second illumination means for emitting illumination; a first sensor means for sensing at least one characteristic of illumination received from the first illumination means concurrently at a plurality of spaced locations along a linear dimension; and a second sensor means for sensing at least one characteristic of illumination received from the second illumination means concurrently at the plurality of spaced locations along the linear dimension. The multi-channel analytical instrument may be summarized as further including a traversing means for moving the first illumination means, the second illumination means, the first sensing means, and the second sensing means relative to the sample holding means, and a traversing means for moving the sample holding means relative to the first illumination means, the second illumination means, the first sensing means, and the second sensing means relative.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIG. 6 is a rear elevational view of the specimen holder assembly, circuit board and optical fibers of FIG. 4.

FIG. 20 is a side elevational view of an analytical instrument in the form of a mass spectrometer, and a microplate removably receivable on the analytical instrument, according to one illustrated embodiment.

DETAILED DESCRIPTION OF THE INVENTION

In the following description, certain specific details are set forth in order to provide a thorough understanding of various embodiments of the invention. However, one skilled in the art will understand that the invention may be practiced without these details.

Unless the context requires otherwise, throughout the specification and claims which follow, the word "comprise" and variations thereof, such as "comprises" and "comprising," are to be construed in an open, inclusive sense, that is as "including, but not limited to."

The headings provided herein are for convenience only and do not interpret the scope of meaning of the claimed invention.

The terms "proximal" and "distal" are used to describe the illustrated embodiments and are used consistently with a description of non-limiting exemplary applications. The terms "proximal" and "distal" are used in reference to a portion of an analytical instrument or specimen or sample holder used with the analytical instrument, unless the context clearly indicates otherwise. It will be appreciated, however, that the illustrated embodiments can be located or oriented in a variety of desired positions.

The terms "specimen holder" and "sample holder" are used interchangeably to describe a container or vessel for at least temporarily containing or holding a substance or material (i.e., specimen or sample) that is the subject of the analytical process. Specimen or sample holders are typically single use, disposable containers. Such are often sealed or include one or more ports which are sealed or sealable. Such may, or may not, include distinct conduits or channels, wells, reservoirs, valves, pumps, electrodes, sensors, or other actuators or transducers. Specimen or sample holders may take a large variety of forms, for example multi-well plates, cuvettes, or microfluidic platforms or microfluidic systems on a chip.

The term "processor-based system" is used herein to denominate systems that include a processor such as a microprocessor, microcontroller, digital signal processors (DSPs), application specific integrated circuit (ASIC), programmed logic controller (PCL), or programmable gate array (PGA) for instance a field programmable gate array (FPGA) or other controllers.

Figure 1:
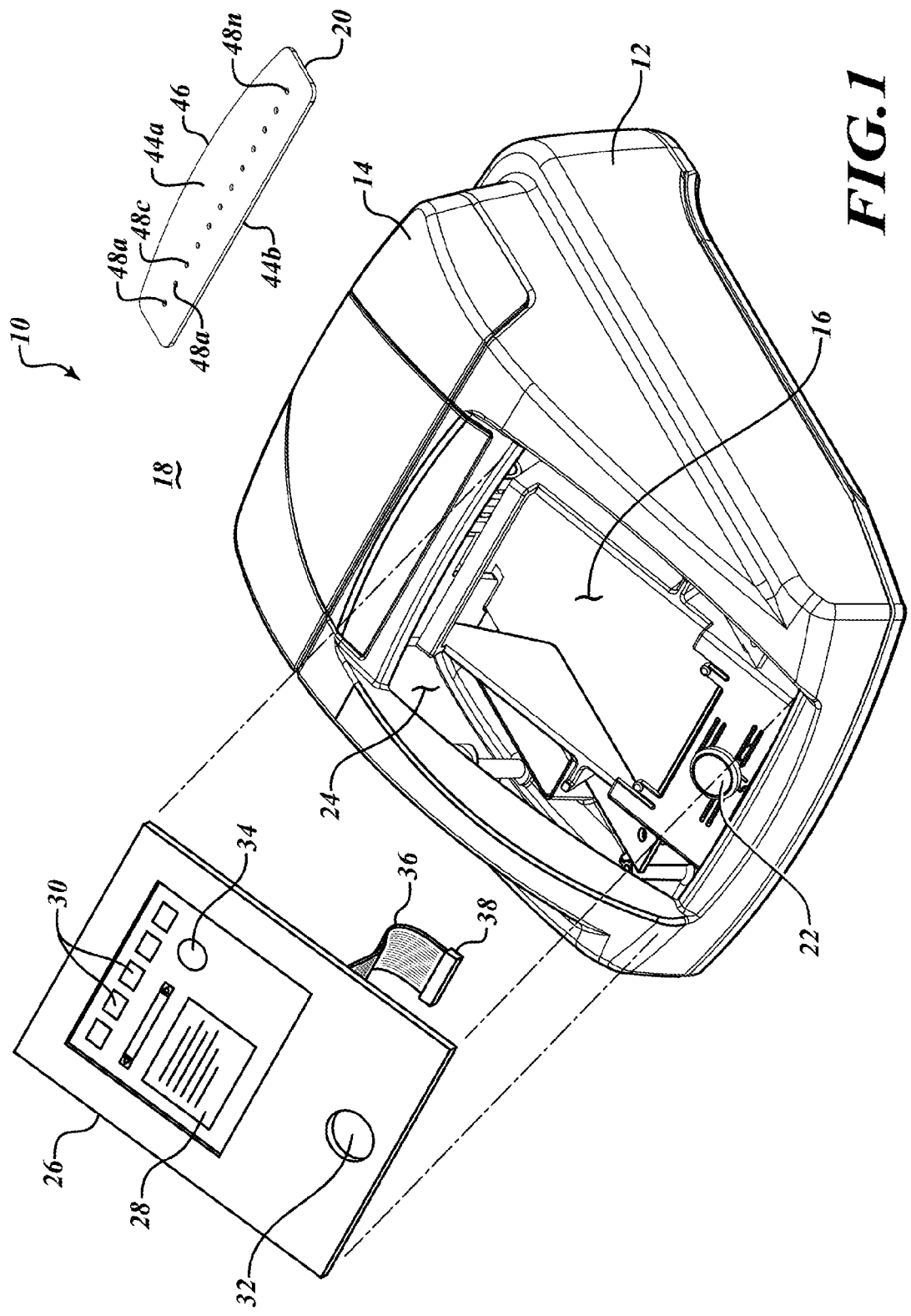
FIG. 1 is a partially exploded isometric view of a housing and display of an analytical instrument in the form of a mass spectrometer, and a specimen holder removably receivable in the housing, according to one illustrated embodiment.
Figure 2:
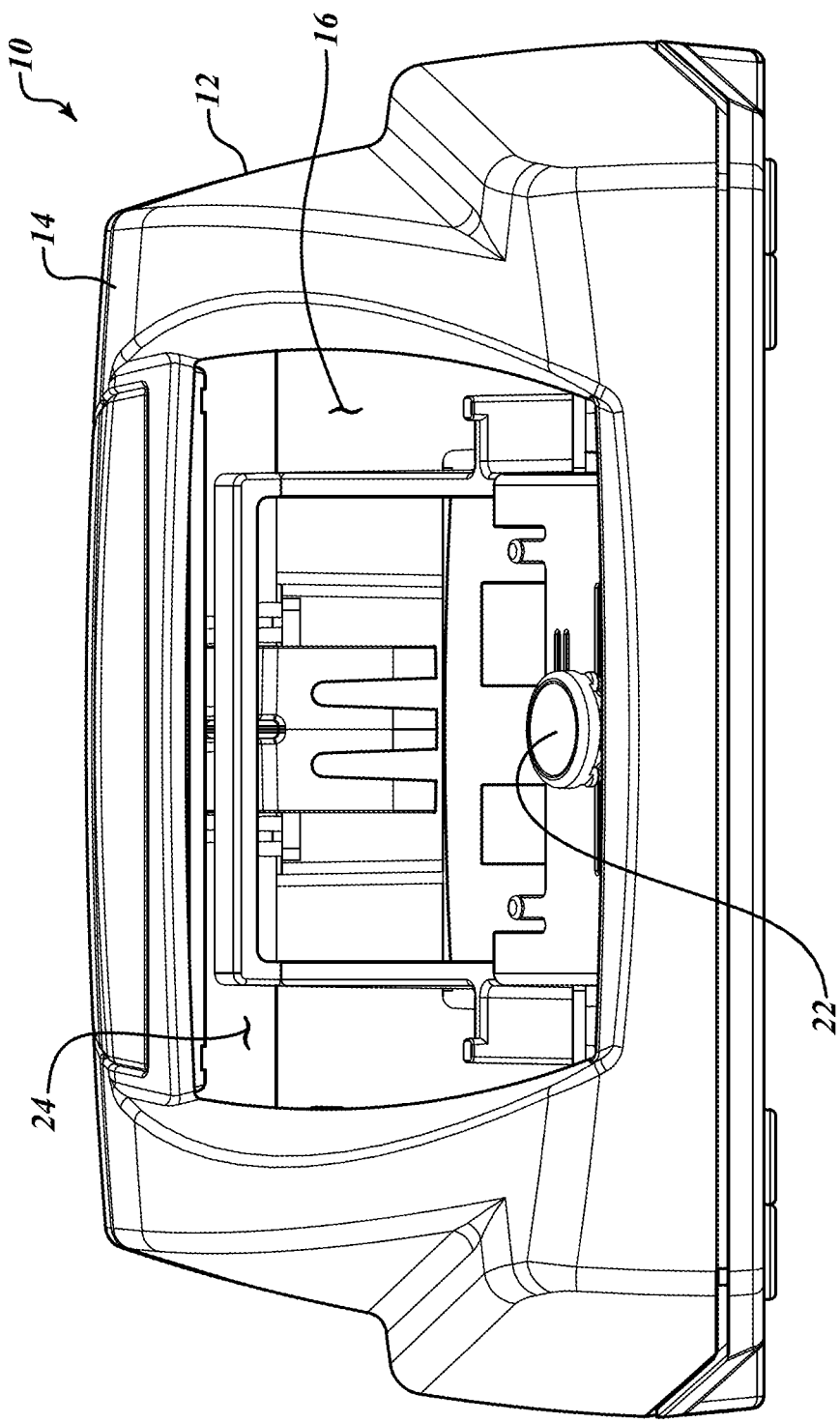
FIG. 2 is a front elevational view of the housing of FIG. 1.
Figure 3:
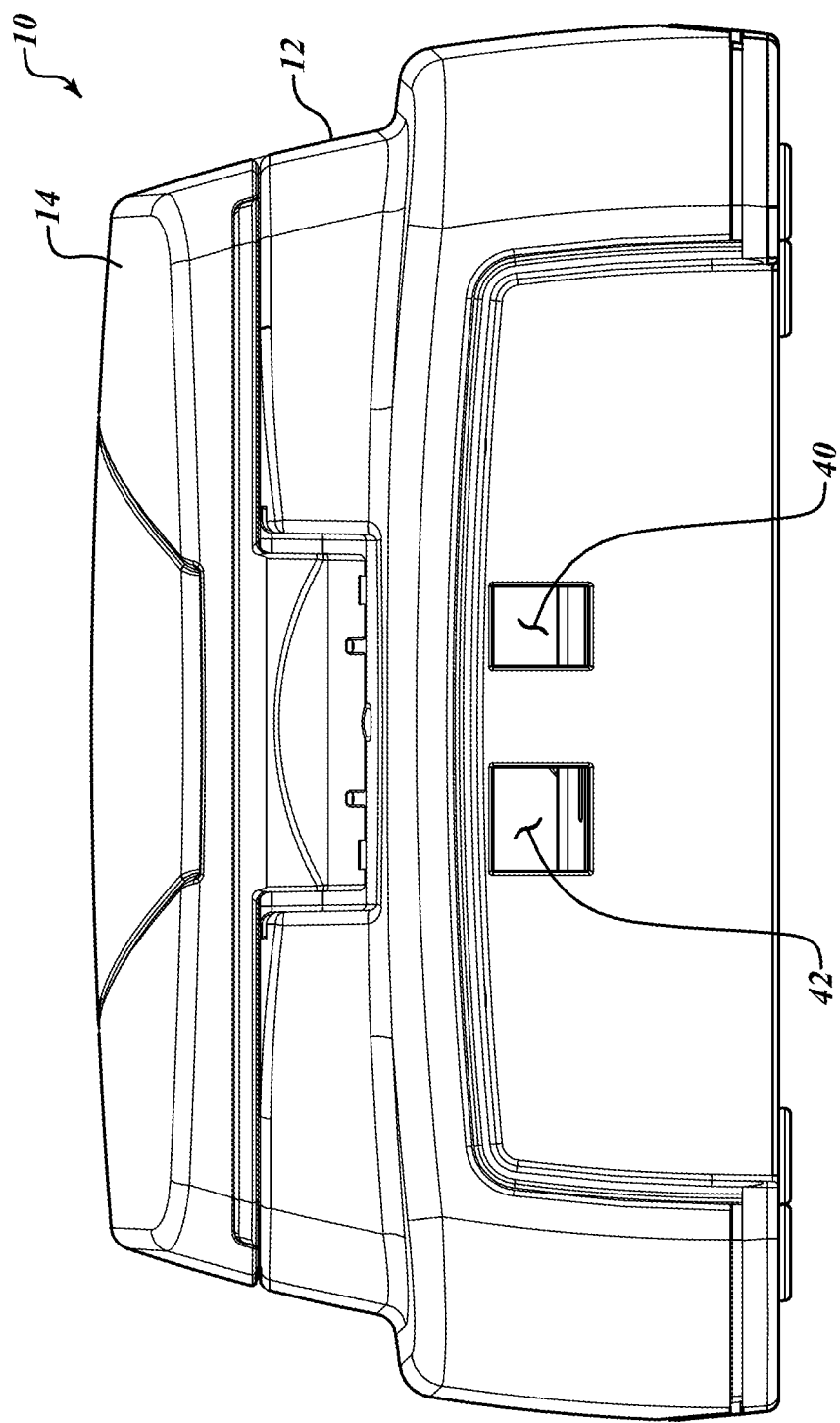
FIG. 3 is a rear elevational view of the housing of FIG. 1.

FIGS. 1-3 show a portion of an analytical instrument 10, according to one illustrated embodiment. The analytical instrument 10 may take a variety of forms, for example a spectrometer.

In particular, FIGS. 1-3 show a housing 12 of the analytical instrument 10. The housing 12 includes a cover 14. The cover 14 is selectively moveable between a closed position or configuration (illustrated in FIGS. 1-3) and an opened position or configuration (not illustrated). The cover 14 may, for example, be pivotally mounted to the rest of the housing 12, allowing the cover 14 to be pivoted between the opened and closed positions or configurations. The opened position or configuration provides access to an interior 16 of the housing 12 from an exterior 18 thereof, allowing placement and retrieval of specimen holders 20 (FIG. 1).

The housing 12 may include a user actuatable button or key 22. User selection or actuation (e.g. pressing or depression) of the user actuatable button or key 22 may cause the analytical instrument to perform a sequence of actions that include illuminating at least portions of the sample holder 20 holding samples or specimens with electromagnetic energy and sensing or detecting responses of the samples or specimens to the electromagnetic energy.

The housing 12 may have an opening 24 to receive a display, for example a liquid crystal display (LCD) panel 26. The LCD panel 26 may be used to present information 28 (e.g., text, data, graphs, analysis, prompts) to a user. The LCD panel 26 may be a touch-sensitive LCD panel, allowing a user to enter information and/or to select various user selectable icons 30 to configure and/or control operation of the analytical instrument 10 via a graphical user interface presented via the LCD panel 26.

The LCD panel 26 or a frame thereof may include an opening 32 to accommodate the user actuatable button or key 22. Alternatively, the user actuatable button or key 22 may be located laterally spaced from the LCD panel 26. As a further alternative, the LCD panel 26 may display an activation or start user selectable icon 34, selection of which may cause the analytical instrument 10 to perform a sequence of actions that include illuminating at least portions of the sample holder 20 holding samples or specimens with electromagnetic energy and sensing or detecting responses of the samples or specimens to the electromagnetic energy. In such an alternative, the physical user actuatable button or key 22 may be omitted.

A cable, for example a ribbon cable 36 with a plug or connector 38, provides communicative coupling between the LCD panel 26 and a control subsystem (not shown in FIGS. 1-3), discussed in detail below.

The housing 12 may include a number of openings to accommodate physical connectors. For example as visible in FIG. 3, the housing 12 may include an opening 40 sized to accommodate a plug or connector to a source of electrical power. For example, the opening 40 may be sized to at least partially receive a connector such as a plug (not illustrated in FIG. 3) from a DC power supply such as an AC/DC rectifier and voltage converter, commonly referred to as a power supply or wall adapter. Also for example, the housing 12 may include an opening 42 sized to accommodate a connector for wired communications. For example, the opening 42 may be sized to at least partially receive a Universal Serial Bus (USB) connector.

Returning to FIG. 1, the specimen holder 20 may take any of a large variety of forms. For example, the specimen holder 20 may take the form of a plate having a pair of opposed major faces, one of which is denominated herein as an upper face 44a and the other as a lower face 44b (faces collectively referenced as 44). The specimen holder 20 may, for example, have a polygonal profile or perimeter 46 (as illustrated in FIG. 1). Alternatively, the specimen holder 20 may, for example, have a circular or oval profile or perimeter, thus may be referred to as a disk (not illustrated). Other shapes or configurations may be employed.

The specimen holder 20 may include a number of distinct specimen or sample holding regions 48a, 48b, 48c-48n (twelve shown, only four called out in FIG. 1, collectively referenced as 48) to hold or retain respective specimens or samples. The specimen or sample holding regions 48 may, for example, take the form of wells, depressions or reservoirs. The specimen or sample holding regions 48 may take other forms of areas or volumes at which specimens or samples of material are retained, for example due to a surface characteristic (e.g., hydrophylicity, hydrophobicity, coating or other material deposition) of the specimen or sample holding regions 48 and/or regions surrounding the specimen or sample holding regions 48. The specimen or sample holding regions 48 may, for example, hold microliters of specimens or samples. For instance, each specimen or sample holding region 48 may hold approximately 0.5 microliters.

At least one of the faces 44, for instance the lower face 44b, of the specimen holder 20 is substantially transparent to at least some wavelengths of electromagnetic energy. In many implementations, the entire specimen holder 20 will be substantially transparent to the various wavelengths of electromagnetic energy that are to be used in performing analysis of the samples or specimens. In at least one implementation, one major face (e.g., the lower face 44b) of the specimen holder 20 is substantially transparent to a set or range of wavelengths while the other opposed major face (e.g., the upper face 44a) of the specimen holder 20 is substantially reflective of the set or range of wavelengths. Such may advantageously reflect electromagnetic energy (e.g., light) back toward a specimen or sample, increasing an amount of illumination of the same.

Figure 4:
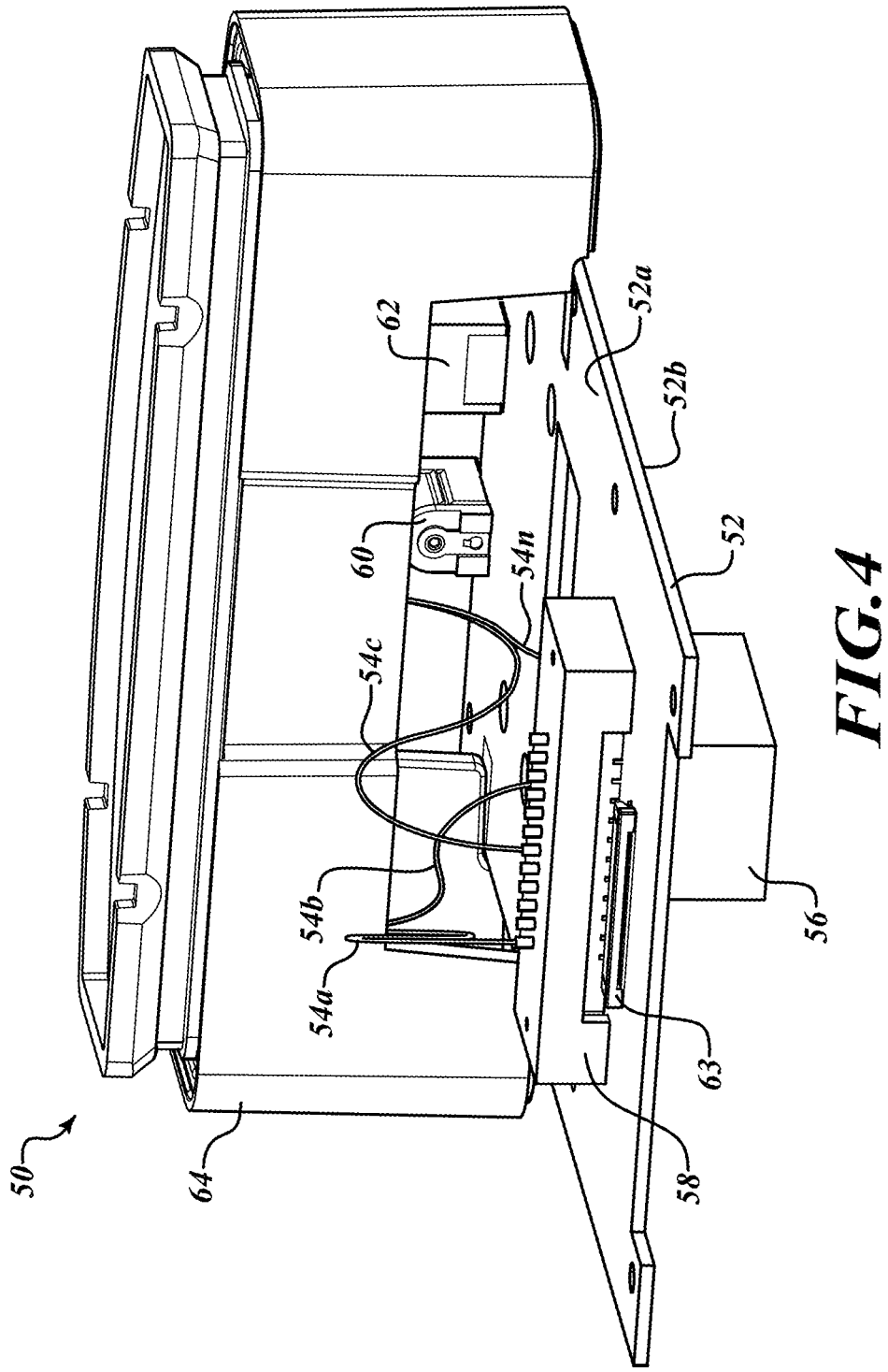
FIG. 4 is an isometric view of a portion of an interior of the mass spectrometer of FIG. 1, particularly illustrating a specimen holder assembly, and a circuit board that carries a number of components including a source of electromagnetic energy, a sensor assembly, and a plurality of conduits such as optical fibers, according to one illustrated embodiment.
Figure 5:
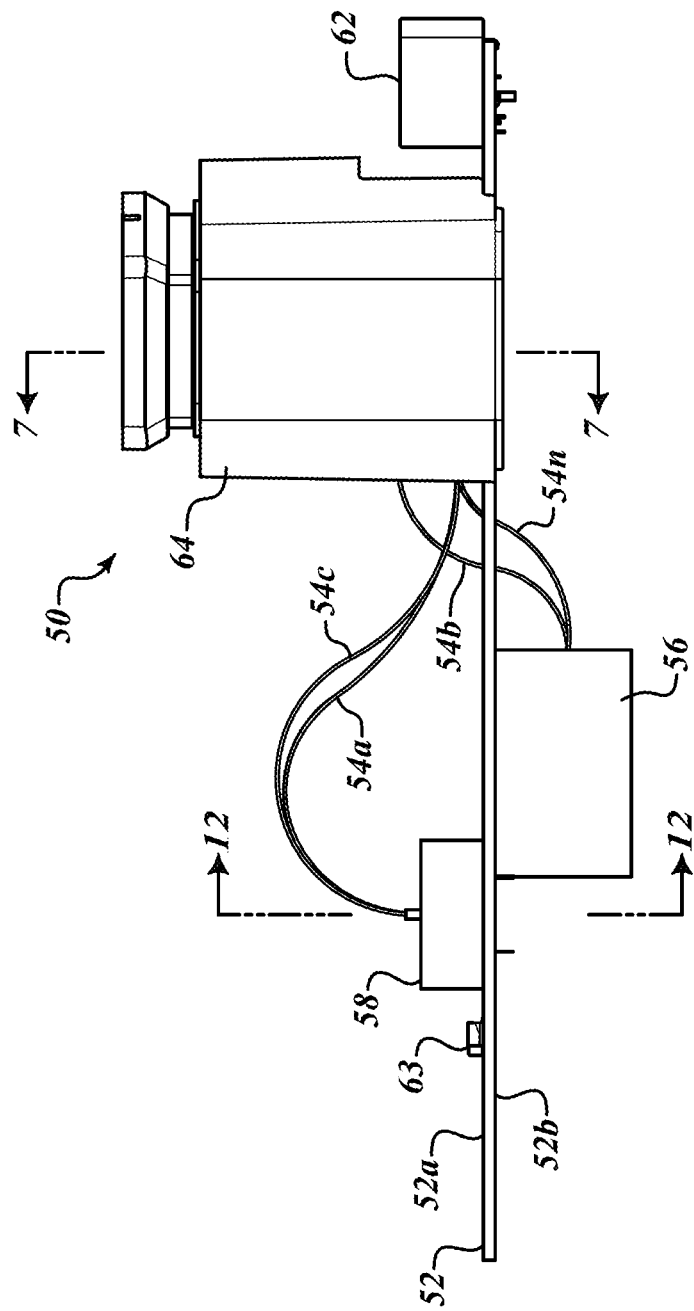
FIG. 5 is a right side elevational view of the specimen holder assembly, circuit board and optical fibers of FIG. 4.

FIGS. 4-6 show an interior portion 16 (FIG. 1) of the analytical instrument 10 of FIG. 1, according to one illustrated embodiment.

The analytical instrument 10 includes specimen holder assembly 50, one or more circuit boards 52 (only one illustrated), and a plurality of optically communicative conduits 54a, 54b, 54c-54n (only four illustrated in FIG. 4, collectively referenced as 54).

The specimen holder assembly 50 receives and holds the specimen holder 20 (FIG. 1). The specimen holder assembly 50 is described in more detail with reference to FIGS. 7-10, below. As described below, the specimen holder assembly 50 aligns specimen or sample holding regions 48 of the specimen holder 20 with respective pairs of the optically communicative conduits 54 (e.g., optical fibers). The specimen or sample holding regions 48 of the specimen holder may be arranged in a one-dimensional or linear array as illustrated, or could be arranged in a two-dimensional array (e.g., 2 by 12, 4 by 16). Notably, the specimen holder 20 may be a consumable article, that is an article intended for a single use and that is disposed of after use.

The circuit board(s) 52 carries various components (e.g., electrical components or electronics) and/or electrically conductive traces. The components may be mounted on either of opposed exterior faces 52a, 52b of the circuit board 52. The electrically conductive traces may be carried on the opposed exterior faces 52a, 52b of the circuit board 52, and/or on layers with the circuit board 52, and/or extending through one or more vias extending through one or more layers of the circuit board 52.

One of the components is at least one source of electromagnetic energy 56 selectively operable to emit electromagnetic energy or radiation at one or more (i.e., ranges) of wavelengths or frequencies. The wavelengths may include wavelengths in the optical portion of the electromagnetic spectrum, for example extending from infrared (IR) or near-infrared (NIR), through the visible portion, to ultraviolet (UV) or near-ultraviolet (NIV), or some portion thereof. The source of electromagnetic energy 56 may include one or more distinct illumination sources. The illumination sources may, for example, be operable to emit electromagnetic energy at respective ranges of wavelengths or frequencies. For instance, one illumination source may emit IR, NIR and red wavelengths while another illumination source may emit UV, NUV and blue wavelengths. Yet a further illumination source may emit wavelengths between red and blue. Any number of illumination sources may be employed. Preferably, the illumination sources are separately actuatable to produce illumination of a variety of desired spectrums. Illumination sources may, for example, comprise light emitting diodes (LEDs), which may take any of a variety of forms (e.g., OLEDs).

The source of electromagnetic energy 56 is optically coupled to the specimen holder assembly 50 via a number of optical conduits 54b, 54n.

One of the components is a sensor assembly 58. The sensor assembly 58 is described in more detail with reference to FIG. 12, below. As described below, the sensor assembly 58 aligns some of the optical fibers (e.g., optical fibers 54a, 54c) with specific areas of a sensor array.

The circuit board 52 also carries a power port 60. The power port 60 may take the form of a connector configured to receive electrical power. For example, the power port 60 may include a jack sized and configured to receive a portion of a plug (not shown). Typically, the power port 60 is configured as a female receptacle to receive direct current (DC) electrical power via a male jack, for instance the jacks found on wall adapters that convert alternating current (AC) electrical power from mains or household electrical receptacle to DC power. In such implementations, power conversion and/or conditioning circuitry may be part of the adapter, housed separately from the housing 12 (FIG. 103). Alternatively or additionally, the power port 60 may include power conversion and/or conditioning circuitry to rectify AC to DC electrical power and/or step-up or step-down voltage, and/or to otherwise condition the electrical power for use on or via the circuit board 52.

The circuit board 52 may also carry one or more communications ports 62 (only one shown). The communications port(s) 62 may take a wide variety of forms, for example those with connectors that permit wired communications connections via various conventional or standard protocols. For example, the communications port(s) 62 may take the form of a female receptacle sized, dimensioned or otherwise configured to receive a conventional male connector (e.g., USB® Type A, USB® Type B, USB® Mini-A, USB® mini-B, USB® micro-A, USB® micro-B, FIREWIRE®, THUNDERBOLT®, RJ45, RJ11).

The circuit board 52 may also carry a connector 63 to accept a complementary plug or connector 38 (FIG. 1) from the LCD panel 26.

FIGS. 7-10 show the specimen holder assembly 50 and optical fibers 54 of FIG. 4, in more detail.

The specimen holder assembly 50 includes a channel stand 64 which supports other components of the specimen holder assembly. The channel stand 64 may having an opening 66 (best illustrated in FIG. 8) in a front portion to allow passage of the optical conduits 54 and may having an opening (visible in FIG. 6) in a rear portion to allow access to various components such as the power port 60 and/or communications port 62 (FIG. 6).

Figure 8:
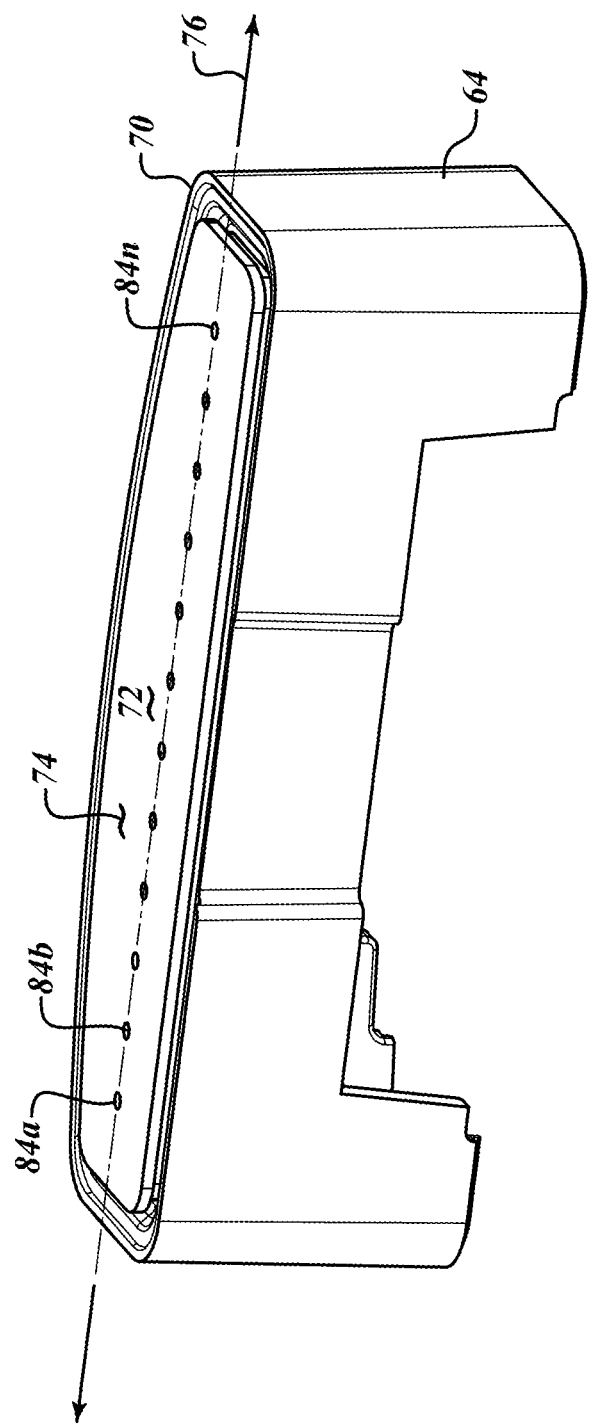
FIG. 8 is a top, front, right side isometric view of a portion of a channel stand of the specimen holder assembly of FIG. 4, which includes a receiver or receptacle to closely removably receive specimen holders.

As best illustrated in FIG. 8, the channel stand 64 has a lip or flange 70 that along with a floor 72 forms a receiver or receptacle 74 to removably receive specimen holders 20 (FIG. 1). The receiver or receptacle 74, and particularly the lip or flange 70 are sized and dimensioned to closely receive the specimen holders 20 (FIG. 1). The lip or flange 70 may be shaped to orient the specimen holder 20 in the receiver or receptacle 74, and to align respective ones of the specimen or sample holding regions 48 of the specimen holder 20 with defined positions of the receiver or receptacle 74. The lip or flange 70 may also be shaped to limit the number of orientations in which the specimen holder 20 can be loaded into the receiver or receptacle 74. For example, the shape of the lip or flange 70 may be nonsymmetrical across a longitudinal axis (double headed arrow 76) thereof, to ensure that the specimen holder 20 can only be loaded in the receiver or receptacle 74 in a single defined orientation.

Figure 7A:
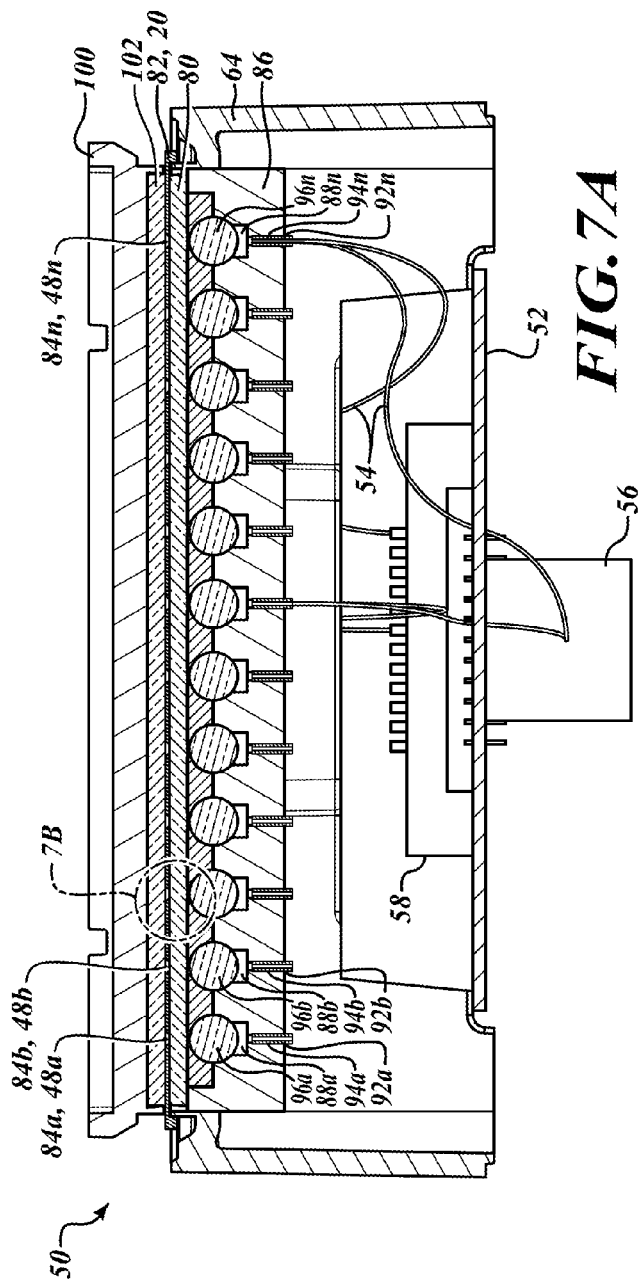
FIG. 7A is a cross-sectional view of the specimen holder assembly and optical fibers of FIG. 4, taken along section line 7-7 of FIG. 5.
Figure 7B:
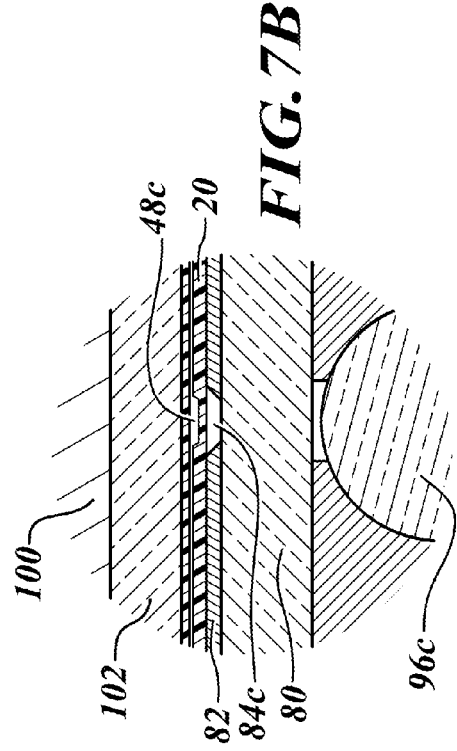
FIG. 7B is an enlarged portion of FIG. 7A, taken at the reference number 7B of FIG. 7A.

As best illustrated in FIGS. 7A and 7B, the floor 72 of the receiver or receptacle 74 may take the form of a transmission plate 80 and a mask 82 that overlies the transmission plate 80.

The transmission plate 80 is substantially transparent to at least some wavelengths of the electromagnetic energy to be used. The transmission plate 80 may, for example, take the form of a glass plate, although other suitable optically transparent materials may be used.

The mask 82 is generally opaque to the electromagnetic energy, except at specific defined positions. The mask 82 may, for example, be formed of a metal or some other generally opaque material, with a number of through-holes 84a, 84b, 84c-84n (FIGS. 8 and 9, twelve shown, four called out, collectively 84) formed therethrough. The through-holes 84 in the mask 82 are positioned, and spaced with respect to one another, to match a positioning, and spacing, of respective ones of the specimen or sample holding regions 48 of the specimen holder 20 (FIG. 1). The through-holes 84 in the mask 82 may be conical, having a relatively more narrow or smaller diameter proximate the transmission plate 80 and relatively wider or larger diameter as the through-holes 84 open into the receiver or receptacle 74. Such may prevent electromagnetic energy (e.g., light) from straying from one of the defined positions toward another one of the defined positions.

Figure 9:
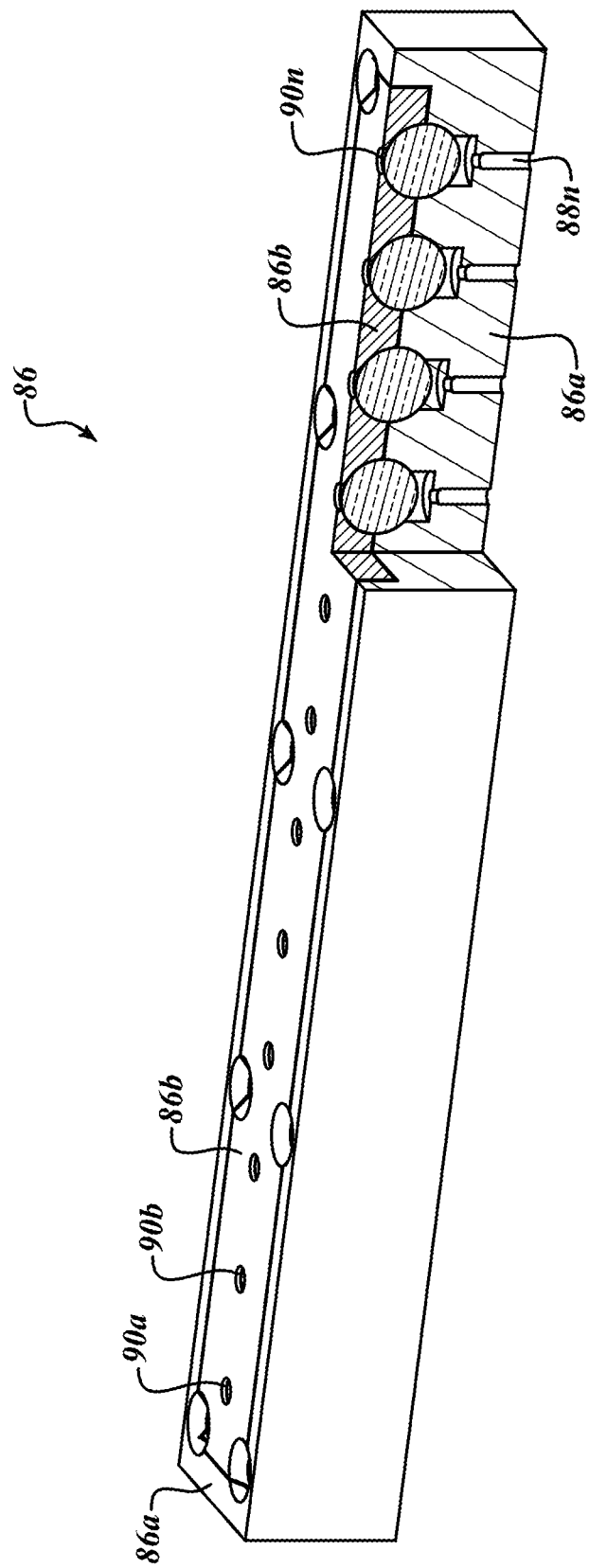
FIG. 9 is partially sectioned top, front, left side isometric view of a lens holder and alignment frame of the specimen holder assembly of FIG. 4, according to one illustrated embodiment.

As best illustrated in FIGS. 7 and 9, the channel stand 64 supports a lens holder and alignment frame 86. The lens holder and alignment frame 86 may include a first portion 86a and a second portion 86b secured to the first portion 86a for example via one or more fasteners (not shown). The lens holder and alignment frame 86 includes a plurality of passages 88a, 88b-88n (twelve shown, only three called out in FIG. 7, collectively 88) which extend through the first and the second portions 86a, 86b, respectively. The passages 88 each have a sample proximate opening 90a, 90b-90n (FIG. 9, twelve shown, three called out, collectively 90) at one end, and a sample distal opening 92a, 92b-92n (FIGS. 7A and 7B, twelve shown, three called out, collectively 92) at another end. The sample proximate openings 90 are spaced with respect to one another to match a spacing of through-holes 84 in the mask 82. Thus, when a sample holder 20 is closely received in the receiver or receptacle 74, the sample proximate openings 90 are aligned with respective ones of the specimen or sample holding regions 48 of the specimen holder 20. The sample distal openings 92 are each coupled to a respective pair of optical fibers 54, via a respective splitter 94a, 94b-94n (FIGS. 7A and 7B, twelve shown, three called out, collectively 94). The splitters 94 may, for example, be 50:50 splitters, splitting the illumination approximately evenly.

The lens holder and alignment frame 86 may hold a number of optical lenses. In particular, the lens holder and alignment frame 86 may advantageously include a number of spherical or ball lenses 96a, 96b-96n (FIGS. 7A and 7B, twelve shown, three called out, collectively 96). A respective spherical or ball lens 96 may be located in an optical path between the sample proximate opening 90 and the sample distal opening 92. For example, each of the passages 88 of the lens holder and alignment frame 86 may securely hold a respective spherical or ball lens 96, for example secured between the first and second portions 86a, 86b. The spherical or ball lenses 96 advantageously achieve a spread of electromagnetic energy which emanates from the sample proximate openings 90 toward samples or specimens in the sample holder 20 which are to be analyzed. For example, the spherical or ball lens may increase a diameter of illumination by 40 times, and increase an area illuminated by 1600 times. For example, the use of spherical or ball lenses 96 increase an area illuminated from 15 μm$^2$ to over 2 mm$^2$.

Figure 10:
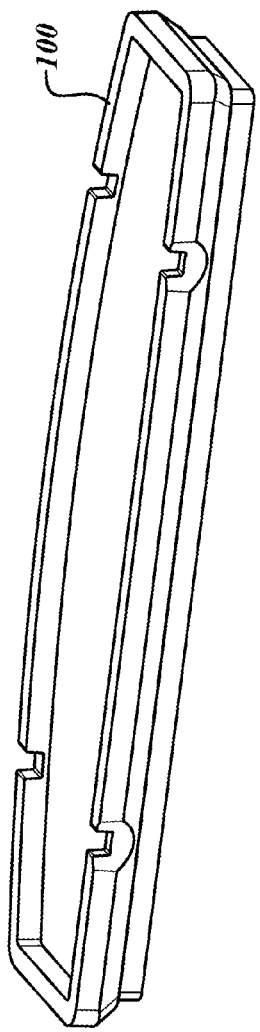
FIG. 10 is a top, front, right side isometric view of a portion of a cover of the specimen holder assembly of FIG. 4.
Figure 11:
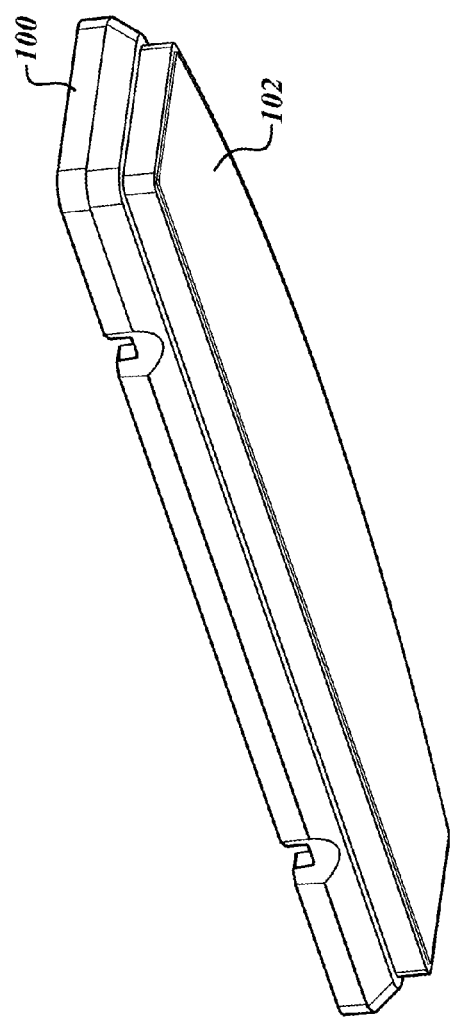
FIG. 11 is a bottom, front, right side isometric view of a portion of a cover of the specimen holder assembly of FIG. 4.

As best illustrated in FIGS. 10 and 11, the specimen holder assembly may include a cover 100.

The cover 100 may be generally shaped in a similar fashion to the shape of the receiver or receptacle 74. The cover 100 includes a mirror or reflector 102 on a bottom surface thereof. Alternatively, the bottom surface of the cover 100 may be highly polished to reflect electromagnetic energy, such as light. In use, the cover 100 overlies the sample holder 20. As best illustrated in FIG. 7B, the mirror or reflector 102 advantageously reflect or otherwise return electromagnetic energy back emanating from the sample proximate openings 90 back toward a specimen or sample in the sample holder 20. Thus, the electromagnetic energy first passes in one direction (i.e., from the sample proximate openings 90 through the specimen or sample holder 20 toward the mirror or reflector 102) and then passes in a second direction (i.e., from the mirror or reflector 102 back through the specimen or sample holder 20 toward the sample proximate openings 90). The mirror or reflector 102 may for example reflect visible light, ultraviolet light, and optionally infrared light dependent on the particular end use application.

Figure 12:
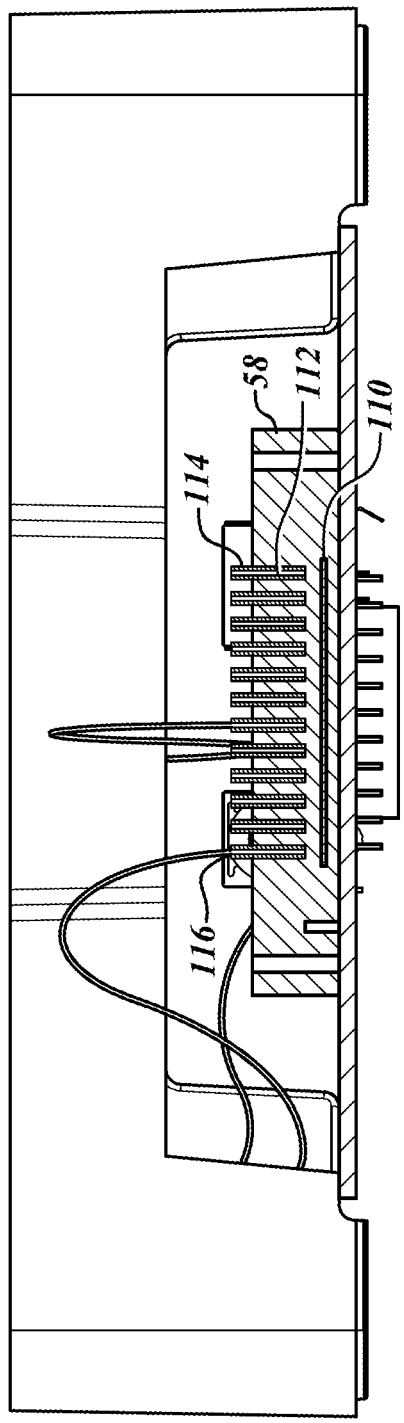
FIG. 12 is a partially cross-sectioned view of the sensor assembly and optical fibers of FIG. 4 taken along section line 12-12 of FIG. 5.

FIG. 12 shows the sensor assembly 58 and optical fibers 54 of FIG. 4 in more detail.

The sensor assembly 58 includes one or more sensors or transducers. For example, the sensor assembly 58 may include a photosensor, for example a charge coupled device (CCD) array 110 or other electromagnetic energy responsive transducer. The CCD array 110 may be a one-dimensional or linear array of CCDs. Such may be particularly suitable where the specimen or sample holding regions 48 are arranged as a linear array. Alternatively, the CCD array 110 may be a two-dimensional array of CCDs. Such may accommodate specimen holders 20 (FIG. 1) where the specimen or sample holding regions 48 are arranged in either one- or two-dimensional arrays. The CCD array 110 may take the form of a global shutter CCD array, operable to concurrently sample multiple or even all elements of the CCD array 110. Thus, the CCD array 110 can sample or capture information from multiple specimens in a specimen holder 20 (FIG. 1) concurrently. Such may optionally be sequentially operated to sample or capture information from multiple specimens in a specimen holder 20 (FIG. 1) sequentially.

The sensor assembly 58 includes a number of passages 112 (twelve shown, only one called out in FIG. 12) having couplers 114 (twelve shown, only one called out in FIG. 12) spaced along a longitudinal axis of the sensor assembly 58. The couplers 114 are sized to receive a terminus portion 116 (one called out in FIG. 12) of one of a respective pair of optically communicative conduits 54. Thus, each of the passages 88 of the lens holder and alignment frame 86 are optically coupled by a respective optically communicative conduit 54 to a respective position along the CCD array 110. Since the position and orientation of the specimen holder 20 is defined relative to the sample proximate openings 90 of the lens holder and alignment frame 86, this ensures that electromagnetic energy from each of the specimen or sample holding regions 48 of the specimen or sample holder 20 is directed to a respective portion of the CCD array 110.

Figure 13:
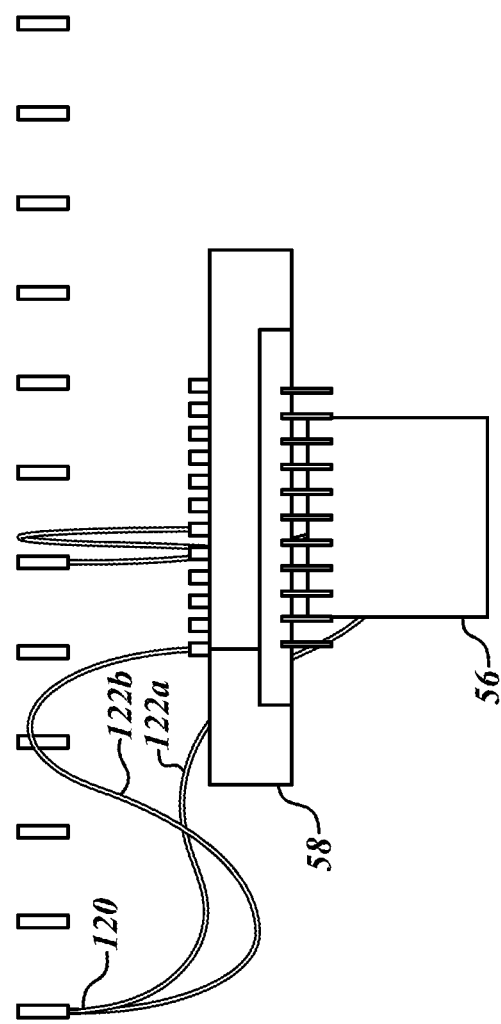
FIG. 13 is an enlarged front elevational view of the specimen holder assembly, circuit board and optical fibers of FIG. 4, particularly illustrating splitters formed by fused portions of respective pairs of the optical fibers, according to one illustrated embodiment.

FIG. 13 shows a number of splitters 120 combining respective ones of pairs of optically communicative conduits 122a, 122b (collectively 122) to implement a multiple channel instrument, according to one illustrated embodiment.

In particular, the analytical instrument 10 may have a number N of channels, each channel corresponding to a respective possible sample. The illustrated embodiments show a twelve-channel analytical instrument 10. However, the analytical instrument may have fewer or greater numbers of channels. The analytical instrument 10 may even have more channels than can be used with a particular specimen holder 20. For example, a sixty-four or ninety-six channel analytical instrument may be capable of operating with a specimen holder 20 (FIG. 1) having only twelve specimen or sample holding regions 48 (FIG. 1), yet also capable of operating with a specimen holder with sixty-four or even ninety-six specimen holding regions. Thus, an analytical instrument 10 may be used with different specimen holders with various numbers of specimen or sample holding regions 48 (FIG. 1), arranged in various arrangements (e.g., one- or two-dimensional arrays, staggered arrays).

For each channel, a respective first optical fiber 122a of a pair 122 may extend between a light source 56 and a respective passage 88 (FIGS. 7A and 7B) of the lens holder and alignment frame 86 to transmit light toward the respective sample. For each channel, a respective second optical fiber 122b of the pair 122 may extend between the respective passage 88 (FIGS. 7A and 7B) of the lens holder and alignment frame 86 and a respective passage 112 (FIG. 12) of the sensor assembly 58 to transmit light toward the CCD array 110. Each of the first and second optical fibers 122a, 122b of a pair 122 may be at least optically coupled, and possibly physically coupled, to the respective passage 88 of the lens holder and alignment frame 86 by a respective splitter 120. The splitters 120 may be formed by fused portions of respective ones of the respective pairs of optical fibers 54.

Figure 14:
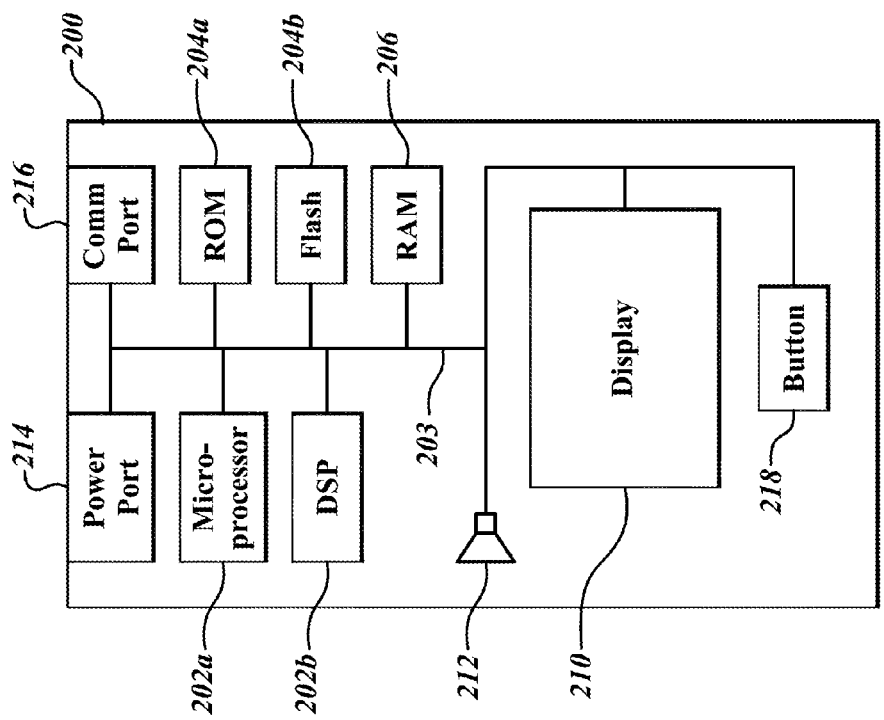
FIG. 14 is a schematic diagram of a processor-based control system of the mass spectrometer of FIG. 1, communicatively coupled to a host computer system via at least one communications channel, according to one illustrated embodiment.

FIG. 14 is a schematic diagram of a processor-based control system 200 of the analytical instrument 10, according to one illustrated embodiment.

The control subsystem 200 may take any of a large variety of forms. Without limiting the alternatives, the control subsystem 200 may include one or more controllers, for example one or more microprocessors 202a, digital signal processors (DSPs) 202b, application specific integrated circuits (ASICS), programmable gate arrays (PGAs), programmed logic controllers (PLCs) (collectively 202), etc. programmed or otherwise configured to control operation of the analytical instrument 10. The controller 202 may be communicatively coupled to one or more nontransitory processor readable media, for instance via one or more buses 203. For example, the controller 202 may be coupled to nonvolatile memory which stores instructions and/or data, for instance read only memory (ROM) 204a or Flash memory 204b (collectively 204). Additionally, or alternatively, the controller 202 may be coupled to volatile memory which stores instructions and/or data, for instance random access memory (RAM) 206. Alternatively, the analytical instrument 10 may omit the controller 200 and memory 204, 206, relying on an external system to control operation thereof.

While illustrated as a single bus 203, in most instances the control subsystem 200 will include two or more buses, for instance one or more electrical power buses of varying voltages, one or more data buses, instruction buses, address buses, etc.

The control subsystem 200 may include a user interface (UI). The UI may, for example include one or more displays, such as an LCD display 210. The UI may include one or more speakers 212, operable to provide audible alerts and possible prompts or instructions to the end user. The UI may include an activation button or key 218, and/or some other switches, keys, or user actuatable buttons or user selectable icons.

An operator can enter commands and information via input devices such as the touch-sensitive LCD display 210 or optionally a physical keyboard or keypad (not shown) and/or a pointing device such as a mouse (not shown), and/or via a graphical user interface displayed via the touch-sensitive LCD display 210. Other input devices can include a microphone, joystick, game pad, tablet, scanner, etc. These and other input devices are connected to one or more of the processing units 202 through an interface such as a serial port interface (not shown) or parallel port (not shown) that couples to the bus 203. Other interfaces such as a wireless interface can be used.

While not shown, the control subsystem 200 may include a number of sensors or transducers to sense, measure or detect various operational conditions or parameters. While also not shown, the control subsystem 200 may include one or more visual indicators that provide a visual indication of an operating condition or state of the analytical instrument 10. For example, one or more of the visual indications may indicate a ready state, a processing state, a completion state, an error state. Visual indicators may, for example, take the form of one or more light emitting diodes (LEDs), for example emitting respective colors to indicated different conditions or states. Alternatively, visual indicators may take other forms, for instance one or more indications on the LCD panel 210.

The analytical instrument 10 may include an electrical power port 214 to supply electrical power to the analytical instrument. The analytical instrument 10 may include a rechargeable power storage device (not shown), for example an array of secondary chemical battery cells, ultra-capacitors or fuel cells.

The analytical instrument 10 may include one or more communications ports 216. The communications port(s) 216 may provide communications with devices external to the analytical instrument 10. The communications ports 216 may include wired as well as wireless ports. For example, the communications ports 216 may include Ethernet ports, Universal Serial Bus (USB) ports, Firewire ports, Thunderbolt ports, etc., and/or ports compliant with various IEEE 802.11 protocols. Such may allow communications with other processor based devices, such as a host computer system (not shown).

The nonvolatile and non-transitory storage media 204, 206 may store computer readable instructions, data structures, program engines and other data for the controllers 202. Program engines can include, for example, a basic input/output system ("BIOS"), an operating system, one or more application programs, other programs or engines and program data.

Those skilled in the relevant art will appreciate that other types of computer-readable storage media that can store data accessible by a computer may be employed, such as hard disks, optical disks, magnetic cassettes, digital video disks ("DVD"), Bernoulli cartridges, smart cards, etc.

The instructions may cause the processor-based control subsystem 200 to control the analytical instrument 10 according to a defined algorithm. For example, the instructions may cause the source of electromagnetic energy 56 to emit selected wavelengths of electromagnetic energy (e.g., light) to illuminate specimens or samples in a specimen holder. Also for example, the instructions may cause the CCD array 110 (FIG. 12) to detect electromagnetic energy returned from the specimens or samples. The instructions may further cause the processor 202 to analyze returned electromagnetic energy, or to otherwise store information characterizing such for later analysis. Analysis of data may include, for example, one or more determining spectral response of a material. Analysis, alerts, corrective actions, suggestive prompts, and related data or information may be stored for future reference, for example stored via nontransitory storage media 204. Collected data representing the operation of the analytical instrument 10, the response of the specimens or samples, and/or characteristics of the illumination, may be stored to the nontransitory storage media 204, for example in one or more data structures, for instance in data structures of a database (e.g., relational database).

Other program engines may include instructions for handling security such as password or other access protection and communications encryption. The system memory 204, 206 may also include communications programs, for example, a server for permitting the control subsystem 200 to provide services and exchange data with other computer systems or devices via the Internet, corporate intranets, extranets, or other networks (e.g., LANs, WANs) as described below, as well as other server applications on server computing systems such as those discussed further herein. The server may be markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers are commercially available such as those from Microsoft, Oracle, IBM and Apple.

The control subsystem 200 can operate in a networked environment using logical connections to one or more remote computers and/or devices. For example, the control subsystem 200 can operate in a networked environment using logical connections to one or more host computer systems (not shown). Communications may be via a wired and/or wireless network architecture, for instance, wired and wireless enterprise-wide computer networks, intranets, extranets, and the Internet. Other embodiments may include other types of communication networks including telecommunications networks, cellular networks, paging networks, and other mobile networks.

Application programs may also include instructions to read and record information that identifies a consumable component (e.g., specimen holder 20). Such may, for example, read and store a unique identifier that uniquely identifies the specimen holder 20. In such embodiments, the analytical instrument 10 may include, or may be communicatively coupled to, a data carrier reader. For example the analytical instrument 10 may optionally include a machine-readable symbol reading subsystem (not shown) to read machine-readable symbols (not shown) carried by the specimen holders 20. The machine-readable symbol reading subsystem may take any of a large variety of forms, for example laser based or scanning machine-readable symbol readers or flood illumination or imaging based machine-readable symbol readers. Alternatively or additionally, the analytical instrument 10 may include a wireless transponder reader or interrogation subsystem to read wireless transponders, for instance radio frequency identification (RFID) transponders carried by the specimen holders 20.

For example, consumable specimen holders 20 (FIG. 1) may have inscribed on, include, carry or bear a machine-readable symbol (not shown) such as a one-dimensional machine-readable symbol (i.e., barcode symbol) or two-dimensional machine-readable symbol (e.g., area or matrix code symbol) which encodes a unique identifier and is readable by a machine-readable symbol reader or subsystem. The machine-readable symbol (not shown) may, for example, be printed on a label and adhered to the specimen holder 20 on an appropriate surface thereof. Alternatively, or additionally, the consumable specimen holders 20 may include, carry or bear a wireless transponder (not shown) such as a passive radio frequency identification (RFID) transponder or tag which encodes a unique identifier and/or other information that is readable by a reader such as an interrogator and/or writeable thereby. The wireless transponder (not shown) may, for example, be formed as a printed circuit trace antenna and integrated circuit component on a tag and adhered to the specimen holder 20 on an appropriate surface thereof. A wireless transponder may provide advantages over machine-readable symbols, for example allowing storage of information, data or conditions after the transponder or tag is applied to the component. Such may also provide for non-line-of-sight reading. Various examples of operation advantageously employing wireless transponders and/or machine-readable symbols are described herein.

Figure 15:
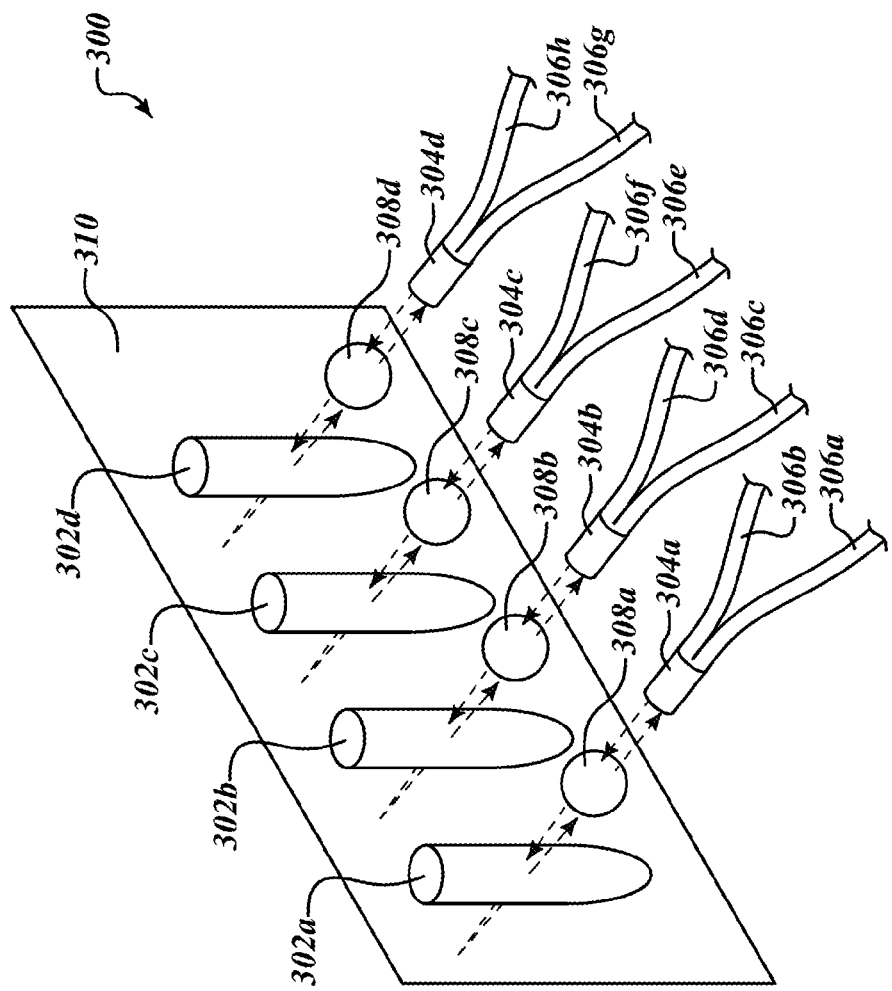
FIG. 15 is a schematic diagram of an analytical instrument in use with a number of cuvette specimen holders, according to another illustrated embodiment.

FIG. 15 schematically shows a portion of an analytical instrument 300 for use with a plurality of cuvettes 302a, 302b, 302c, 302d (collectively 302) which hold specimens or samples, according to one illustrated embodiment.

Similar to previously described embodiments, the analytical instrument 300 illustrated in FIG. 15 employs a plurality of splitters 304a, 304b, 304c, 304d (collectively 304) to optically couple pairs of fiber optics 306a:306b; 306c:306d; 306e:306f; 306g:306h, one fiber optic 306a, 306c, 306e, 306g of each pair coupled to a light source (not shown in FIG. 15) and the other fiber optic 306b, 306d, 306f, 306h of each pair coupled to a sensor (not shown in FIG. 15).

The splitters 304 are optically coupled to respective ones of spherical or ball lenses 308a, 308b, 308c, 308d (collectively 308). Illumination emanating from the spherical or ball lenses 308 first passes through the respective cuvette 302 and specimen held thereby, reflects from a mirror or reflector 310 then again passes through the cuvette and specimen held thereby. This may advantageously increase the amount of illumination to which the specimen or sample is exposed. The returned illumination then passes through the spherical or ball lenses 308 and is returned to the sensor (not shown) via the respective splitter 304.

Other arrangements to accommodate other styles of specimen or specimen holders are of course possible. While the mirror or reflector 310 is shown as a single mirror or reflector, some embodiments may employ more than one mirror or reflector.

Figure 16:
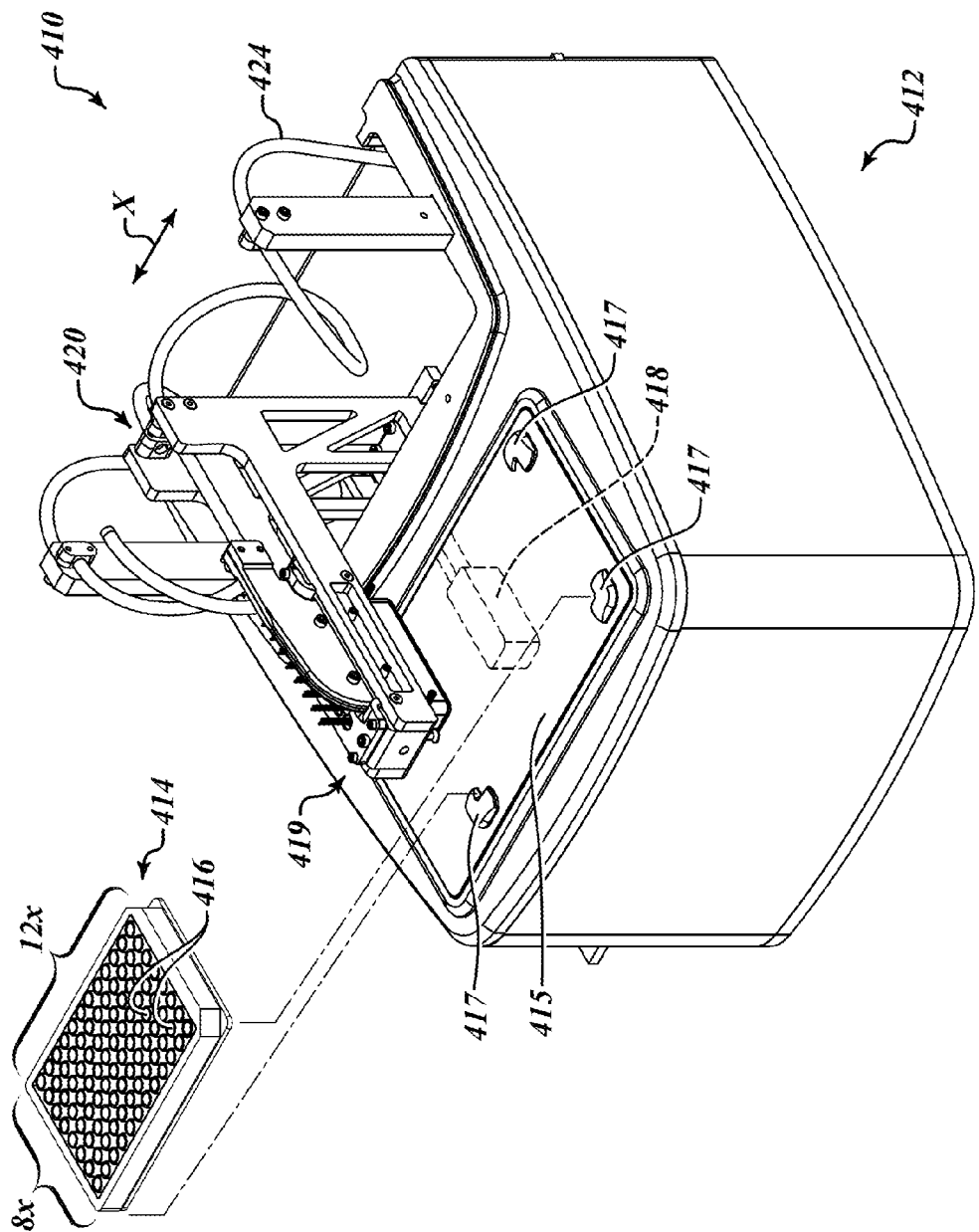
FIG. 16 is an isometric view of an analytical instrument in the form of a mass spectrometer, and a microplate removably receivable on the analytical instrument, according to one illustrated embodiment.
Figure 17:
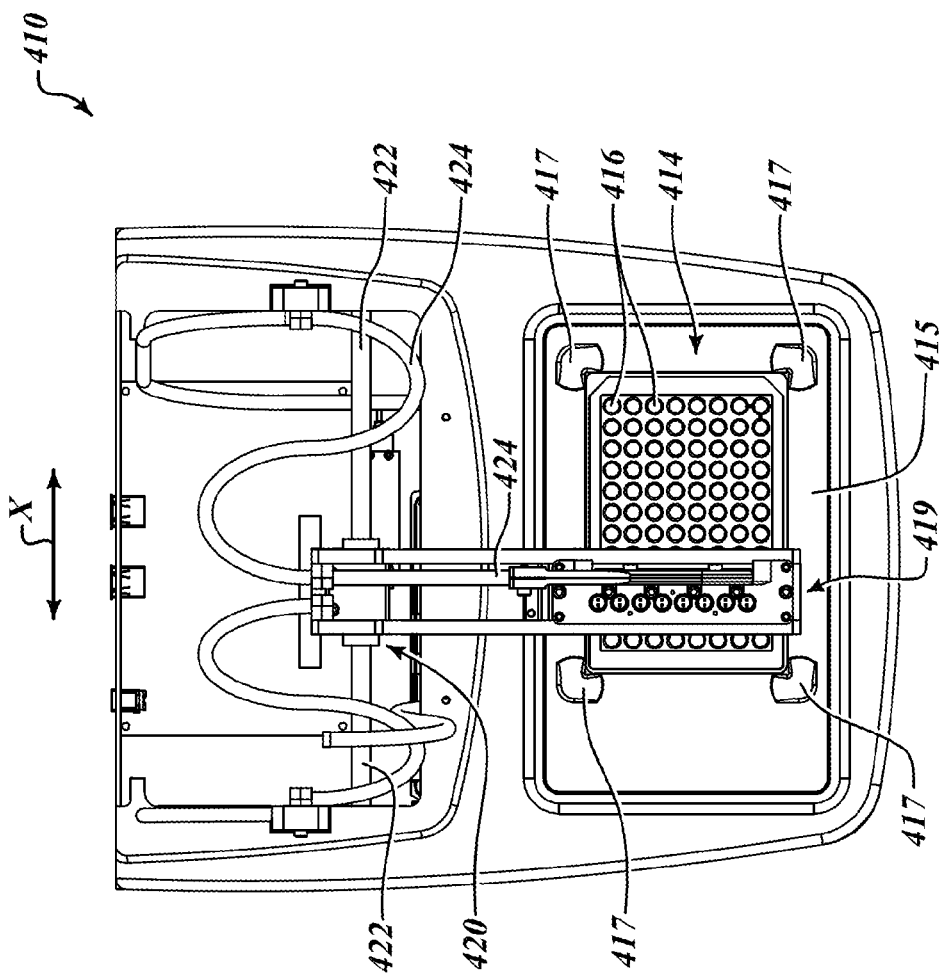
FIG. 17 is a top plan view of the analytical instrument of FIG. 16.
Figure 18:
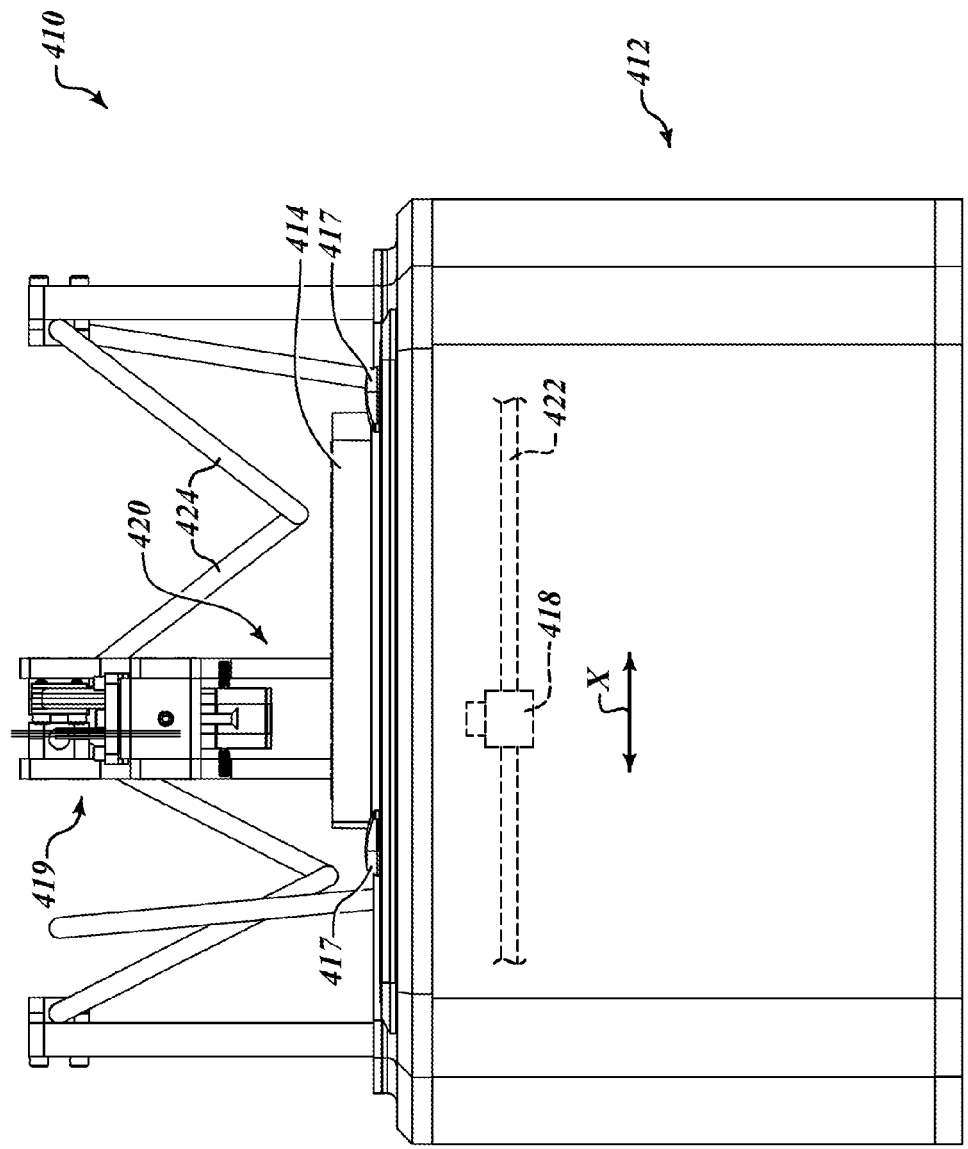
FIG. 18 is a front elevational view of the analytical instrument and microplate of FIG. 16.
Figure 23:
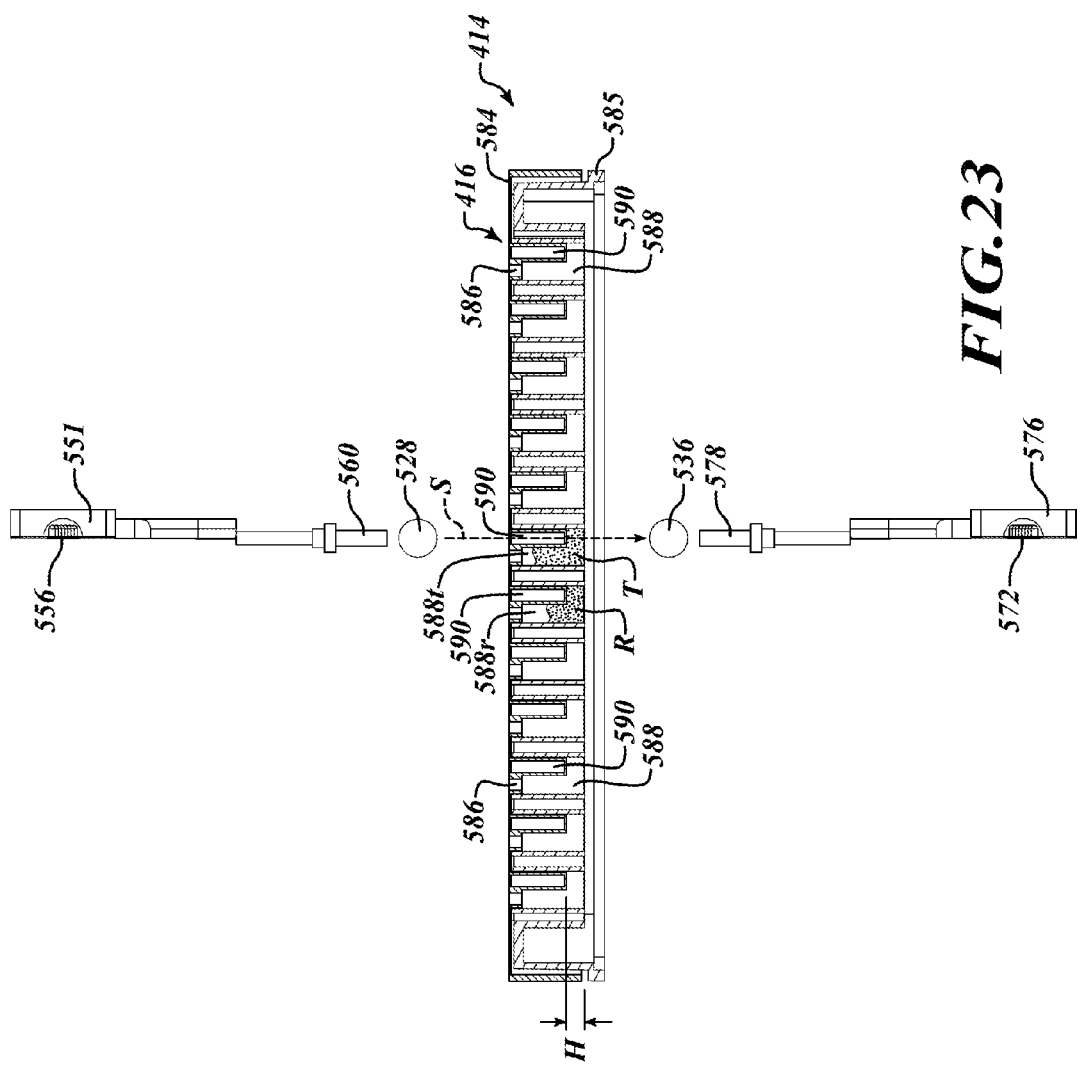
FIG. 23 a front view of FIG. 22, showing a cross-sectioned view of the microplate.

FIGS. 16-19 show an analytical instrument 410, according to one illustrated embodiment. The analytical instrument 410 may take a variety of forms, for example a spectrometer. In particular, FIG. 16 shows the analytical instrument 410 having a housing 412 configured to image and scan a plurality of specimens in a plurality of passes along rows of specimens. A receiver or microplate 414 includes a plurality of wells 416 that each have or receive a specimen (FIG. 23). The microplate 414 shown has 8 rows and 12 columns of wells 416. The housing 412 includes a transmission plate 415 to receive and support the microplate 414. The transmission plate 415 allows at least some wavelengths of electromagnetic energy to be emitted through the transmission plate 415 when operating the analytical instrument 410. The transmission plate 415 includes four corner brackets 417 to receive corners of the microplate 414 to properly align and position the microplate 414 (FIG. 17).

Figure 19:
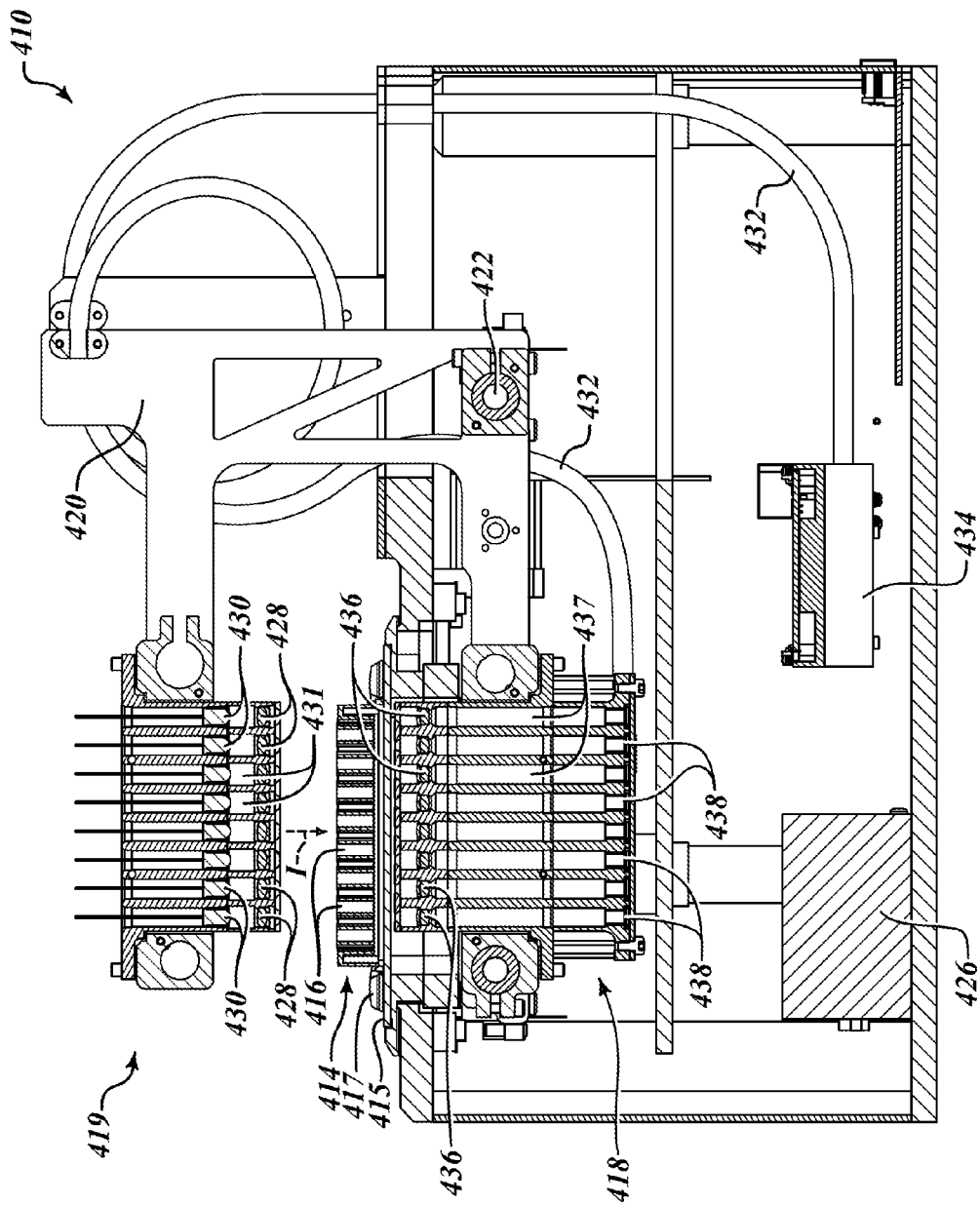
FIG. 19 is a cross-sectioned view of the analytical instrument and microplate of FIG. 16 taken along section line 19-19 of FIG. 18.

The housing 412 further includes an illumination source mount 419 and an illumination sensor mount 418. The illumination source mount 419 is positioned on one side of the microplate 414 and the illumination sensor mount 418 is positioned on the other side of the microplate 414 (FIG. 19). For purposes of illustration, the illumination sensor mount 418 is shown on FIGS. 16 and 18 as a simple shadow box (see FIG. 19 for a detailed illustration of the sensor mount 418). As discussed further below, the illumination source mount 419 includes components operable to emit electromagnetic energy through specimens in each of the plurality of wells 416 in a direction toward the illumination sensor mount 418. The illumination sensor mount 418 includes components operable to receive the electromagnetic energy after being emitted through the specimens in the plurality of wells 416 for ultimate analysis of the electromagnetic energy after it is emitted through the specimens in the wells 416. The illumination sensor mount 418 may be coupled to sensors and image capturing devices for scanning and imaging of the specimens for analysis, as further discussed below.

With continued reference to FIGS. 16-19, the housing 412 includes a carriage 420 coupled to the illumination source mount 419 and the illumination sensor mount 418. The carriage 420 may be a U-shaped member that supports the illumination source mount 419 and the illumination sensor mount 418. The carriage 420 is slidably coupled to a guide member 422 extending horizontal and parallel to a longitudinal axis of the microplate 414. The carriage 420 is movable along the guide member 422 in both directions of the X-axis, as depicted by Arrows X. The carriage 420 may be moved along the guide member 422 by at least one motor (not shown), which may be controlled to regulate the direction and speed of the carriage 420 during operation of the analytical instrument 410. Accordingly, the illumination source mount 419 and the illumination sensor mount 418 are collectively movable with the carriage 420 along the x-axis of the plurality of wells 416 so that the analytical instrument 410 can analyze a plurality of specimens in multiple rows and columns of the microplate 414. In the example shown, 96 wells having specimens can be analyzed during a single working operation of the analytical instrument 410, as further discussed in the present disclosure.

In some aspects and with continued reference to FIG. 19, the illumination source mount 419 includes eight spherical or ball lenses 428 (4 called out) arranged in a row and disposed on a first side of the microplate 414 and above the microplate 414, for example. The illumination source mount 419 may include eight LEDs 430 (4 called out) arranged in a row relative to respective ball lenses 428. The LEDs 430 may be coupled to an electrical connection for illumination of the LEDs 430, or the LEDs 430 could be removed and replaced with optical fibers coupled to a light source, such as a light source 426, for illumination of light through the ball lenses 428. The light source 426 may be the same or similar as the source of electromagnetic energy described with reference to FIGS. 1-15. Eight illumination channels 431 (2 called out) are positioned between the ball lenses 428 and the LEDs 430, respectively. The LEDs 430 and the ball lenses 428 may be securely held in place by the illumination source mount 419. The ball lenses 428 advantageously achieve a spread of electromagnetic energy which emanates to the specimens in the microplate 414. For example, the spherical or ball lens may increase a diameter of illumination by 40 times, and increase an area illuminated by 1600 times. For example, the use of ball lenses 428 increase an area illuminated from 15 µm$^2$ to over 2 mm$^2$.

The illumination sensor mount 418 is coupled to a fiber line 432 that is coupled to a spectrophotometer 434. A spectrophotometer is a device that is able to determine, depending on the control or calibration, what substances are present in a specimen and exactly how much, through calculations of observed wavelengths received by the spectrophotometer. The light that is emitted via the illumination source mount 419 to the specimens in the microplate 414 is imaged by a plurality of sensors 438. Accordingly, the illumination sensor mount 418 may include eight spherical or ball lenses 436 (4 called out) arranged in a row and disposed on a second side of the microplate 414 and below the microplate 414, for example. Eight sensor channels 437 (2 called out) are positioned adjacent the ball lenses 436 at respective positions along the row of ball lenses 436. Each ball lens 436 is positioned at a corresponding position relative to each ball lens 428 of the illumination source mount 419. Thus, a pair of ball lenses includes one ball lens 436 and a respective ball lens 428 that are in an optical path with each other and with a respective well 416 of the microplate 414.

The plurality of sensors 438 may be positioned below the ball lenses 436 on the second side of the microplate 414 to capture images of a respective specimen in the microplate 414. The sensors 438 are arranged in a row and positioned respective to the ball lenses and the sensor channels 437. The sensors 438 may each include one of a charge-coupled device and a complementary metal-oxide-semiconductor to capture images of the illuminated specimens in the microplate 414. Each sensor 438 may be electrically coupled to a control module of the spectrophotometer 434 for analysis of the image captured by each sensor 438. Thus, in 12 passes, the analytical instrument 410 can image 96 specimens, for example. This provides the advantage to scan a plurality of specimens in a very short period of time compared to the time it takes for existing systems to perform the same functions.

FIG. 20 shows an analytical instrument 510, according to one illustrated embodiment, and FIGS. 21-26 show components coupled to the analytical instrument 510 shown in FIG. 20. The analytical instrument 510 may take a variety of forms, for example a spectrometer. In this example, the analytical instrument 510 positions a bundle of illumination emitting optical fibers above a microplate and emits energy through only one optical fiber through only one specimen at a time, as compared to eight at one time with reference to FIG. 19. The analytical instrument 510 of FIG. 20 provides a means to image and scan a plurality of specimens at a time. As such, it includes an assembly of scanning devices in mount 516 (FIG. 21) and an assembly of imaging devices also in mount 516 (FIG. 21A).

Figure 21:
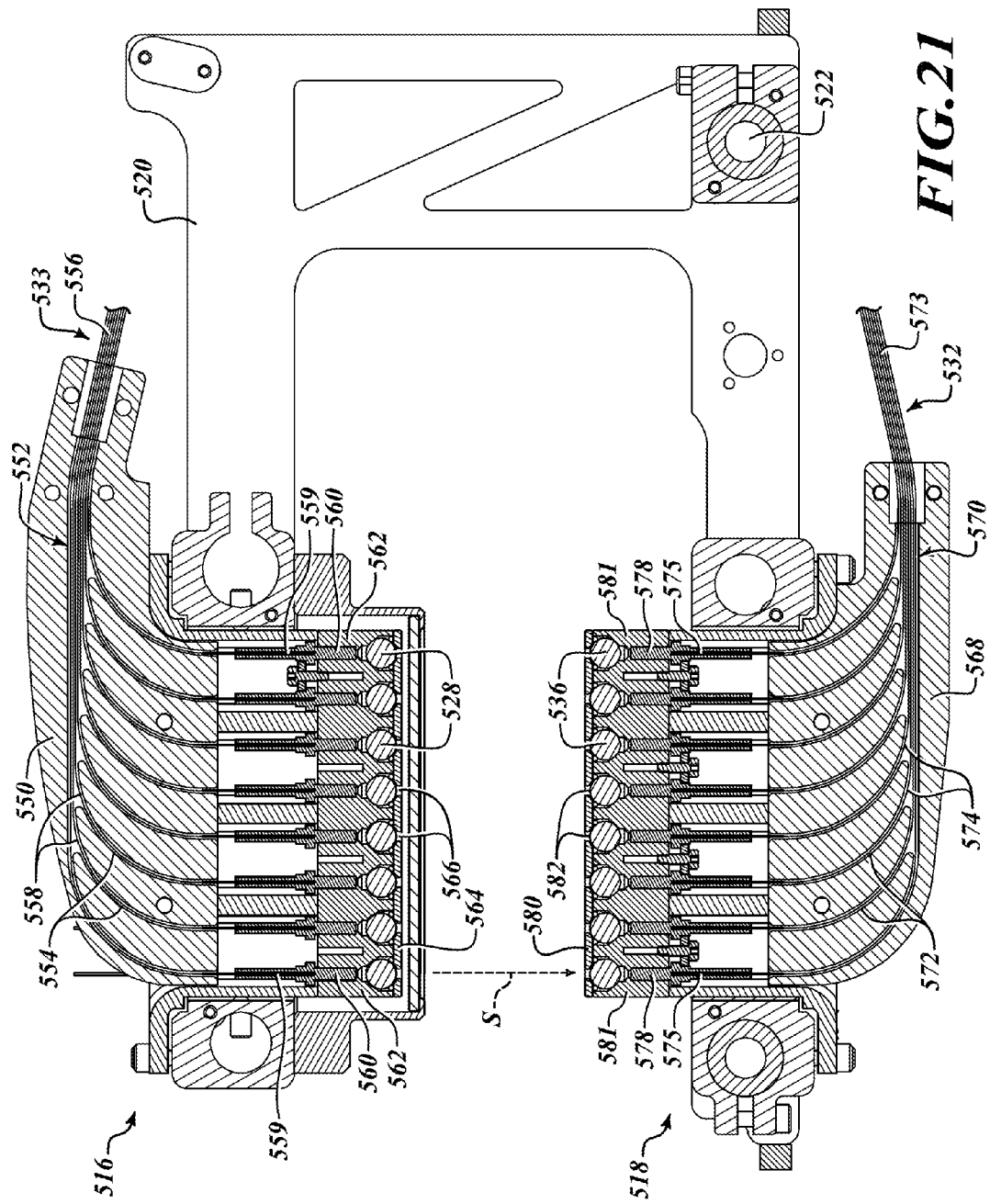
FIG. 21 is a cross-sectioned view of FIG. 20A taken along lines 21-21.

The analytical instrument 510 includes a frame 512 to support components of the analytical instrument 510 (a housing may be provided to enclose the components, such as the housing of FIG. 16). A carriage 520 is coupled to the frame 512 and includes an illumination source mount 516 and an illumination sensor mount 518 (FIG. 21). The carriage 520 may be movable along a guide member 522, such as described with reference to FIGS. 16-19. A microplate 414 is positioned between the illumination source mount 516 and an illumination sensor mount 518. A transmission plate 415 may be positioned below the receiver or microplate 414 and allow at least some wavelengths of electromagnetic energy to be emitted through the transmission plate 415. The transmission plate 415 includes corner brackets 417 to receive corners of the microplate 414 to properly align the microplate 414 (such as shown in FIG. 17).

Figure 24:
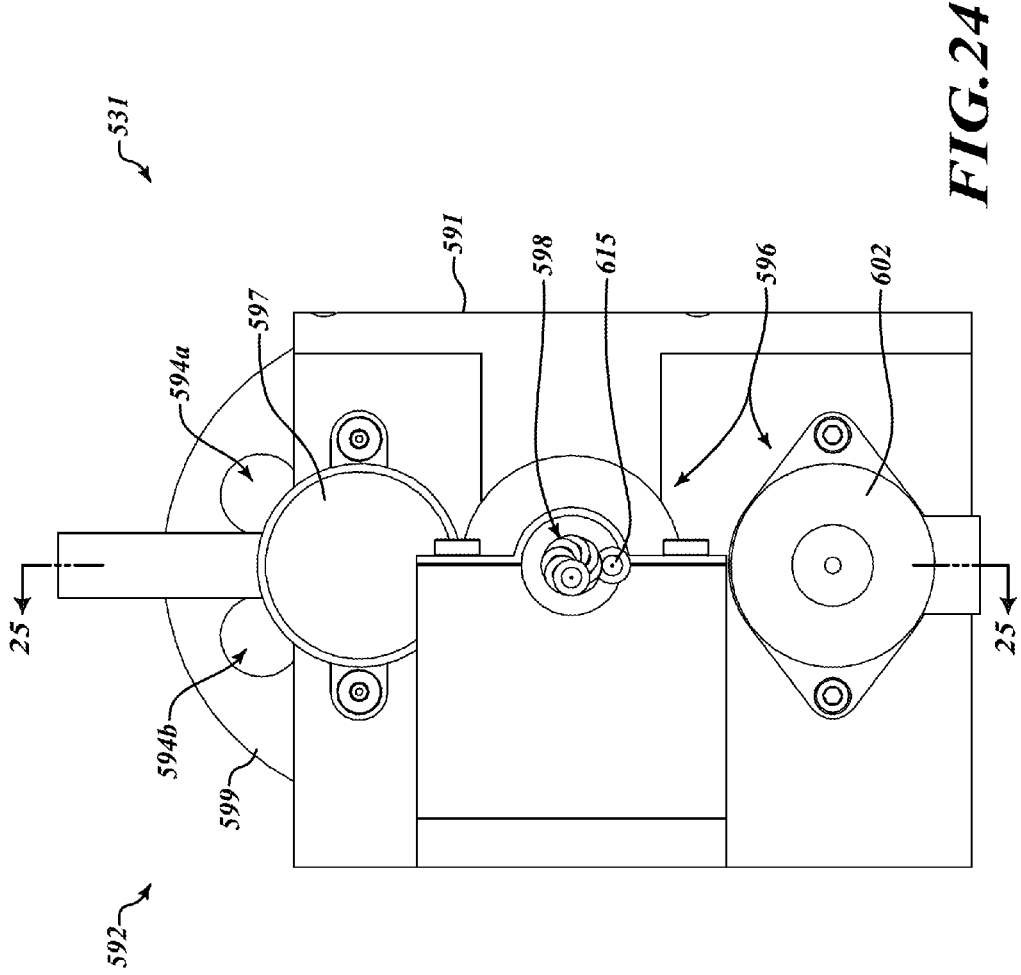
FIG. 24 is a front elevational view of the light source module of FIG. 20.
Figure 25:
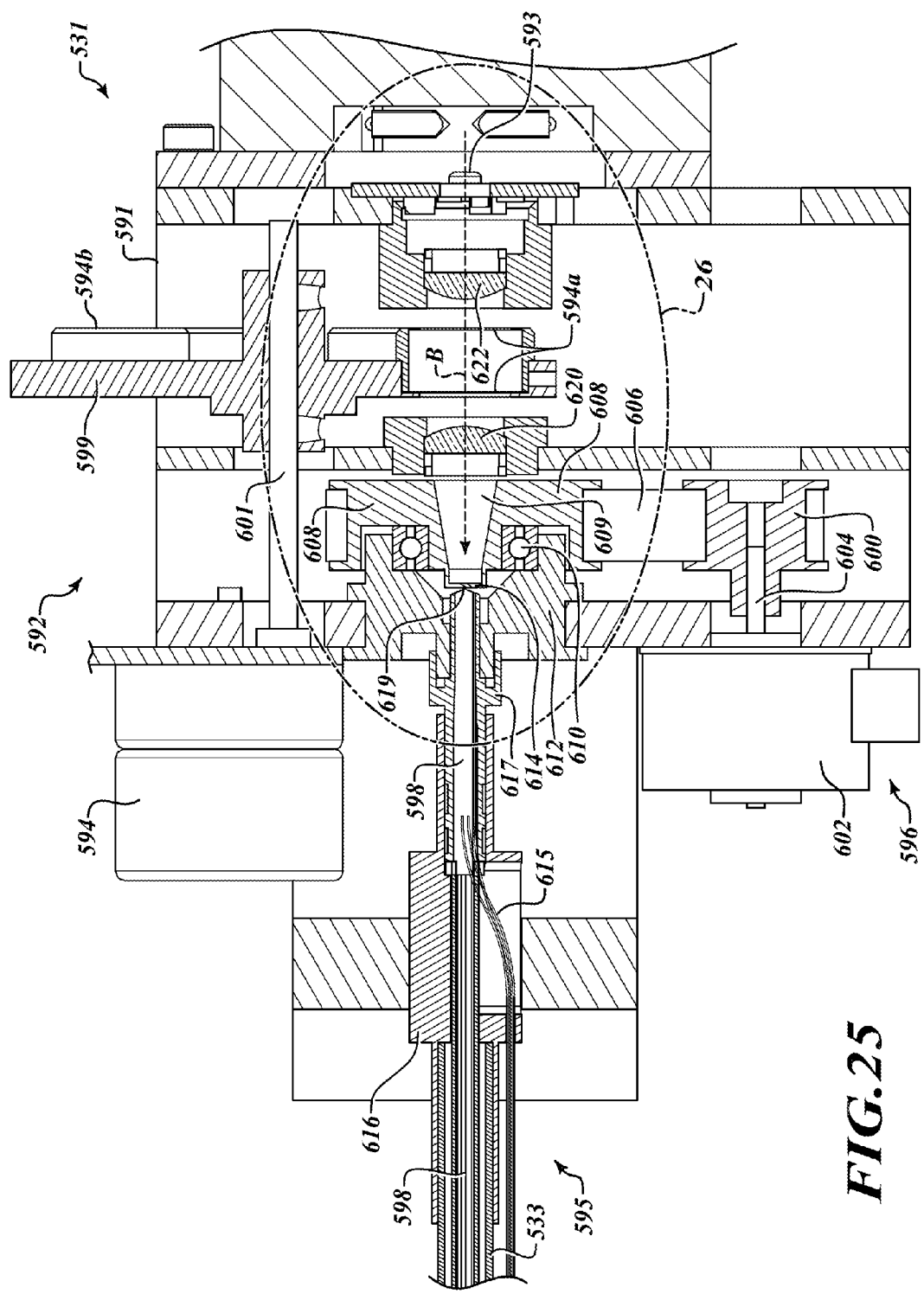
FIG. 25 is a cross-sectioned view of the light source module of FIG. 20, taken along lines 25-25 of FIG. 24.

The analytical instrument 510 includes a light source module 531 coupled to a fiber line 533 (FIGS. 24 and 25). The fiber line 533 is coupled to the illumination source mount 516. The analytical instrument 510 includes a spectrophotometer 534 coupled to a fiber line 532. The fiber line 532 is coupled to the illumination sensor mount 518 (FIG. 21). The fiber lines 532 and 533 each include a plurality of optical fibers 556, 572.

Figure 20A:
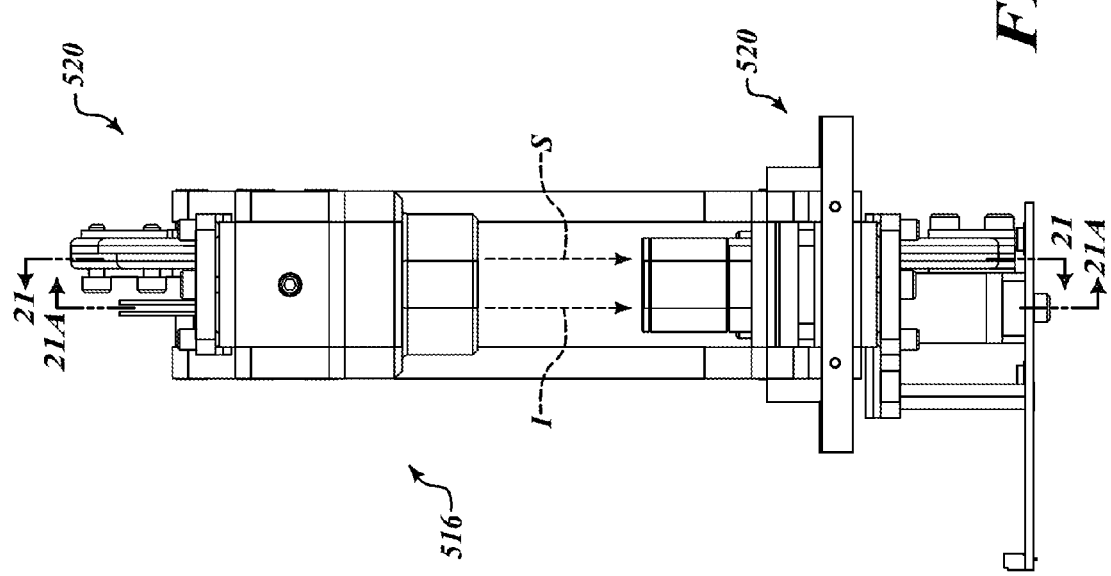
FIG. 20A is a front elevational view of a portion of the analytical instrument of FIG. 20.
Figure 21A:
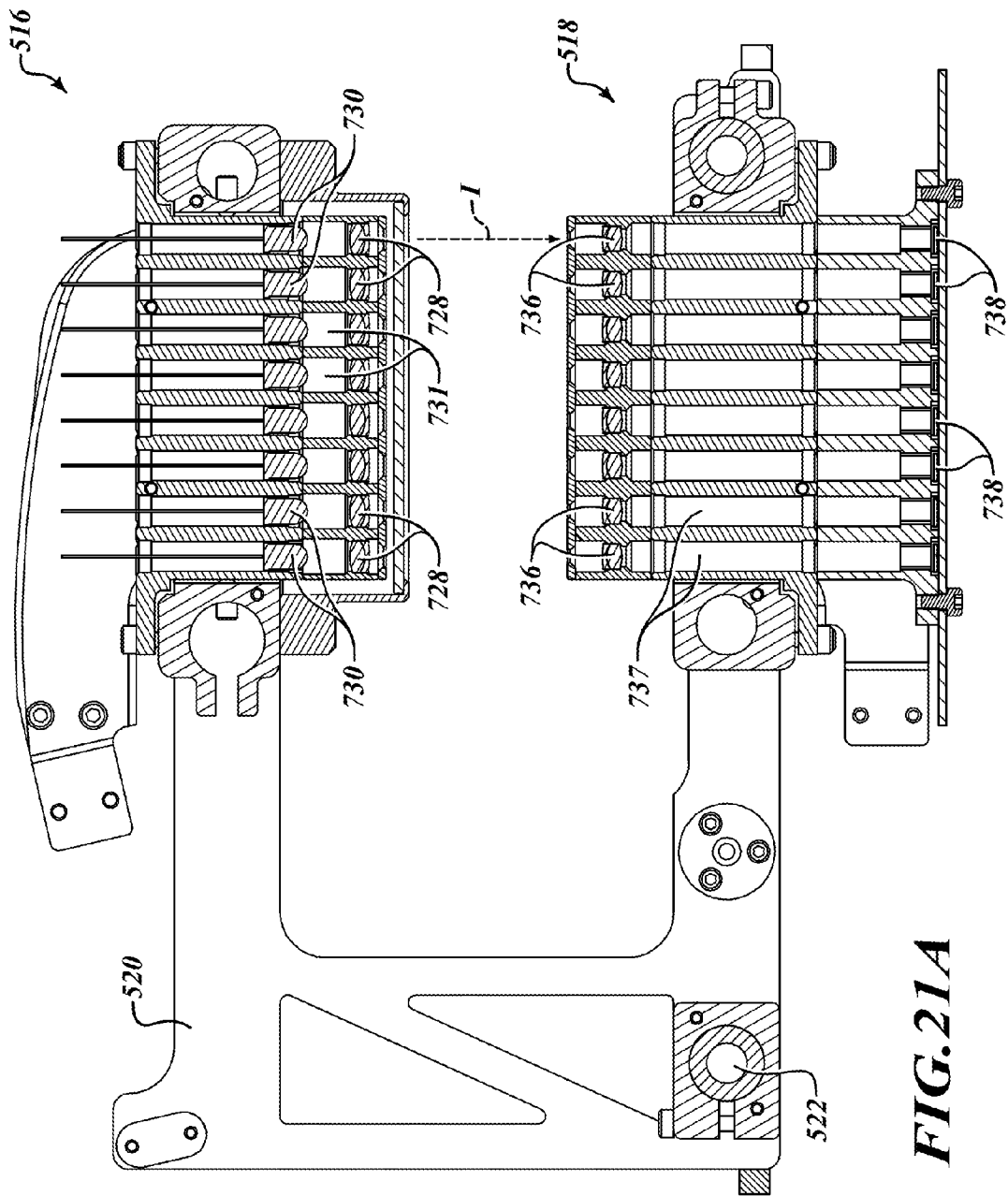
FIG. 21A is a cross-sectioned view of a portion of the analytical instrument of FIG. 20 taken along lines 21A-21A.

FIG. 20A shows a front view of the carriage 520 of FIG. 20 supporting the illumination source mount 516 and the illumination sensor mount 518. The illumination source mount 516 and the illumination sensor mount 518 are configured to scan a plurality of samples and image a plurality of samples at the same time. This is illustrated by the scanning path S and the imaging path I.

Figure 22:
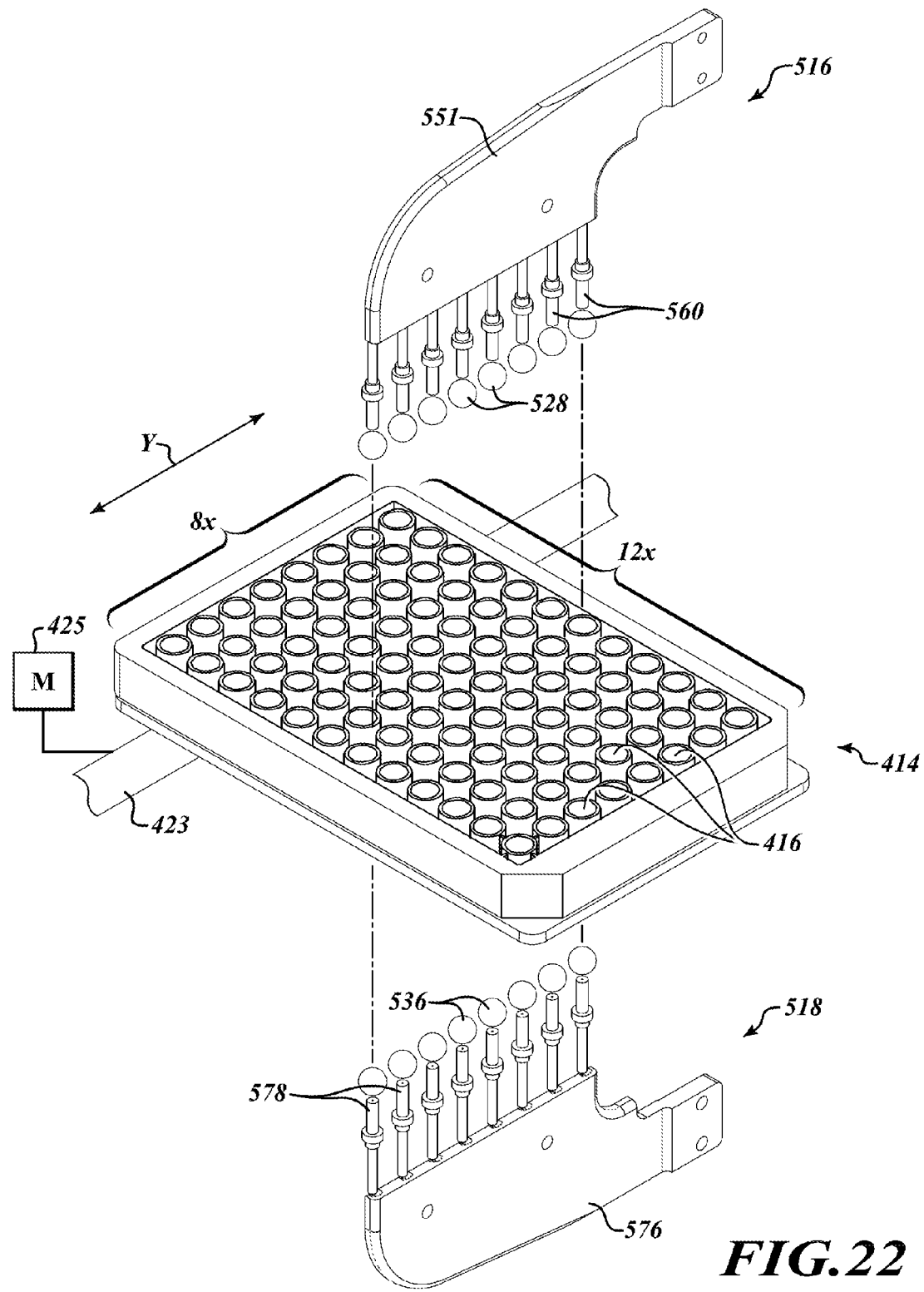
FIG. 22 is an isometric view of a portion of the analytical instrument of FIG. 20.

FIG. 21 shows a cross sectioned view of the carriage 520 supporting the illumination source mount 516 and the illumination sensor mount 518 taken along lines 21-21 of FIG. 20A, and FIG. 21A shows a cross sectioned view of the carriage 520 supporting the illumination source mount 516 and the illumination sensor mount 518 taken along lines 21A-21A of FIG. 20A. FIG. 21 shows the illumination source mount 516 having a housing plate 550 that includes a main channel 552 having eight fiber channels 554 (2 called out) extending individually from the main channel 552. The main channel 552 includes a plurality of optical fibers 556 in a fiber bundle, which are connected to the light source module 531 shown on FIG. 20. The plurality of optical fibers 556 include eight optical fibers 558 (2 called out) extending from the fiber bundle and contained in the fiber channels 554 of the housing plate 550. A corresponding housing plate 551 may be coupled to the housing plate 550 to contain the optical fibers 558 (FIG. 22 shows only the corresponding housing plate 551).

The optical fibers 558 each have a distal end 559 coupled to respective fiber connectors 560 (2 called out). The fiber connectors 560 are arranged in a row and may be removably coupled to the illumination source mount 516 by fasteners. The optical fibers 558 are positioned adjacent respective ball lenses 528 (2 called out) by respective fiber connectors 560. The illumination source mount 516 may include a lens mount 562 having individual areas to secure the ball lenses 528 and position the fiber connectors 560 adjacent the ball lenses 528. The illumination source mount 516 may include an illumination plate 564 coupled to the lens mount 562 and positioned below the ball lenses 528 opposite the distal ends 559 of the optical fibers. The illumination plate 564 may include eight apertures 566 proximate respective lenses 528 to focus and allow passage of light therethrough. Thus, the light source module 531 emits electromagnetic energy in a particular wavelength to the optical fibers 558, to the ball lenses 528 and to the illumination sensor mount 518 in a direction depicted by Arrow S. Such emission of light may occur only through one fiber 558 and ball lens 528 at a time, or through multiple fibers 558 and ball lenses 528 at a time, depending upon the light source and system requirements.

Similarly, the illumination sensor mount 518 includes a housing plate 568 that includes a main channel 570 having eight fiber channels 572 (2 called out) extending from the main channel 570. The main channel 570 includes a plurality of optical fibers 573 in a bundle, which may be connected to the spectrophotometer 534 shown on FIG. 20. The spectrophotometer 534 may be a theater style spectrophotometer. The plurality of optical fibers 573 include eight optical fibers 574 (2 called out) contained in respective fiber channels 572. A corresponding housing plate 576 (FIG. 22) may be coupled to the housing plate 568 to contain the fibers 574 (FIG. 21). The optical fibers 574 have respective distal ends 575 coupled to respective fiber connectors 578 (2 called out). The fiber connectors 578 may be removably coupled to the illumination sensor mount 518 by fasteners. The distal ends 575 of the optical fibers 574 are positioned adjacent respective ball lenses 536 (2 called out) in respective fiber connectors 578. The illumination sensor mount 518 may include a lens mount 581 to secure the ball lenses 536 and position the fiber connectors 578 adjacent the ball lenses 536. The illumination source mount 516 may include an illumination plate 580 positioned adjacent and above the ball lenses 528. The illumination plate 580 may include eight apertures 582 at respective positions to the ball lenses 528 to focus and allow emission of light to the ball lenses 528 from the opposing ball lenses 528.

Thus, the light source module 531 (FIG. 20) emits electromagnetic energy in a particular wavelength to the fibers 558, the ball lenses 528, specimens, the ball lenses 536, and the fibers 574, and ultimately to the spectrophotometer 534 for analysis of the energy emitted through the specimens (FIG. 20). Such emission and scanning of energy may occur through use of only one pair of corresponding fibers and ball lenses at a time, or through multiple pairs of fibers and ball lenses at a time.

With continued reference to FIG. 21A, the illumination source mount 519 includes eight spherical or ball lenses 728 (4 called out) arranged in a row and disposed on a first side of the microplate 414 and above the microplate 414 (FIG. 20). The illumination source mount 519 may include eight LEDs 730 (4 called out) arranged in a row relative to respective ball lenses 728. The LEDs 730 may be coupled to an electrical connection for illumination of the LEDs 730, or the LEDs 730 could be removed and replaced with optical fibers coupled to a light source, such as the light source module 531, for illumination of light through the ball lenses 728. The LEDs 730 could be white light LEDs, or any color of LED. Eight illumination channels 731 (2 called out) are positioned between the ball lenses 728 and the LEDs 730, respectively. The LEDs 730 and the ball lenses 728 may be securely held in place by the illumination source mount 519. The ball lenses 728 advantageously achieve a spread of electromagnetic energy which emanates to the specimens in the microplate 414. For example, the spherical or ball lens may increase a diameter of illumination by 40 times, and increase an area illuminated by 1600 times. For example, the use of ball lenses 728 increase an area illuminated from 15 µm² to over 2 mm².

The illumination sensor mount 518 includes eight spherical or ball lenses 736 (4 called out) arranged in a row and disposed on a second side of the microplate 414 and below the microplate 414, for example. Eight sensor channels 737 (2 called out) are positioned adjacent the ball lenses 736 at respective positions along the row of ball lenses 736. Each ball lens 736 is positioned at a corresponding position relative to each ball lens 728 of the illumination source mount 519. Thus, a pair of ball lenses includes one ball lens 736 and a respective ball lens 728 that are in an optical path with each other and with a respective well 416 of the microplate 414.

A plurality of sensors 738 may be positioned below the ball lenses 736 on the second side of the microplate 414 to capture images of a respective specimen in the microplate 414. The sensors 738 are arranged in a row and positioned respective to the ball lenses and the sensor channels 737. The sensors 738 may each include one of a charge-coupled device and a complementary metal-oxide-semiconductor to capture images of the illuminated specimens in the microplate 414. Each sensor 738 may be electrically coupled to a control module of the spectrophotometer 734 for analysis of the image captured by each sensor 738. Thus, the spectrophotometer 734 performs spectrum scanning of eight specimens while the sensors 738 simultaneously perform image scanning of eight specimens, all in one pass. Thus, in 12 passes, the analytical instrument 510 can scan and image 96 specimens. Of course, any size microplate could be used to scan dozens of specimens at a time. This provides the advantage to scan and image a large number of specimens, such as 96 specimens, in a very short period of time compared to the time it takes for existing systems to perform the same functions.

FIG. 22 shows a partially exploded perspective view of components of the illumination source mount 516 and the illumination sensor mount 518 with a microplate 414 positioned therebetween. The housing plate 551 of the illumination source mount 516 assists to contain and position optical fibers coupled to the fiber connectors 560 positioned adjacent the ball lenses 528 to place the optical fibers 558 in an optical path with the ball lenses 528 (FIG. 21). The housing plate 576 of the illumination sensor mount 518 assists to contain and position optical fibers coupled to the fiber connectors 578 positioned adjacent the ball lenses 536 below the microplate 414 to place the optical fibers 574 in an optical path with the ball lenses 528.

The microplate 414 includes a plurality of wells 416 (3 called out). The microplate 414 may include 8 rows and 12 columns of wells, comprising 96 wells, for example. The 8 rows correspond to the two sets of eight ball lenses 528, 536. As discussed further in the present disclosure, the analytical instrument 510 is configured to illuminate and scan 8 specimens in 8 wells of one column of the microplate 414 in a single pass with use of the illumination source mount 516 and illumination sensor mount 518. The analytical instrument 510 is further configured to move the illumination source mount 516 and illumination sensor mount 518 to a different column of the 12 columns for illumination and scanning of 8 additional specimens. This process may be repeated in 12 passes of 12 rows until all 96 specimens in the 96 wells are analyzed. This process is accomplished without having to remove the microplate or replace specimens in wells between scanning of one or more columns of specimens. This provides the advantage of scanning dozens of specimens in a very short time period compared to existing systems, which may only scan one specimen or one row of specimens before having to replace the specimens or specimen holders and restart the scanning process.

In some aspects, the microplate 414 is mounted to a guide member 423 and a motor 425 operable to move the microplate 414 horizontally along the y-axis, as depicted by Arrow Y. Accordingly, the carriage 420 (FIG. 16) and the carriage 520 (FIG. 20) is movable along the x-axis and the microplate 414 is movable along the y-axis so that the analytical instrument 410, 510 can analyze specimens in 384 wells or 1536 wells or more, for example.

FIG. 23 shows a rear elevational view of FIG. 22, showing a cross-sectioned view of the microplate 414. The microplate 414 has a means to control the height of specimens to be analyzed for standardization, which improves the accuracy of the imaging and scanning of each specimen. Because each specimen typically will have different heights when positioned in a standard specimen holder or receiver, it is desirable to standardize the height for each specimen in each well of a microplate to improve accuracy of specimen analysis.

In some aspects, the microplate 414 includes an upper frame 584 and a lower frame 585 coupled to each other with the upper frame 584 overlying the lower frame 585. The upper frame 584 includes specimen openings 586 (2 called out) to allow insertion of a specimen into a respective specimen cavity 588 in each well 416. The upper frame 584 includes chambers 590 positioned adjacent a respective specimen cavity 588 in each well 416. The vertical length of the chambers 590 is selected such that the space of the specimen cavity 588 directly below each chamber 590 is at a height H. This provides a standard height H of each specimen to be scanned in respective specimen cavities 588, as depicted by the path of Arrow S through the specimen cavity 588 directly below the chamber 590. This height standardization of specimen measurement may be illustrated by specimen R and specimen T in respective specimen cavities 588r and 588t. As shown, specimen R has a smaller volume than specimen T, which would normally provide a shorter height of specimen R in a typical specimen holder. However, the height of both specimen S and specimen R that will be measured directly below respective chambers 590 will be the same height H due to the position and length of the chambers 590 and the position of the microplate 414 relative to the energy path depicted by Arrow S. Thus, regardless of the volume of each specimen, each specimen will have the same height to be measured in the microplate 414. In some aspects, height H may be 2 mm or 3 mm, or may vary depending upon the requirements of the specimens and system.

Figure 26:
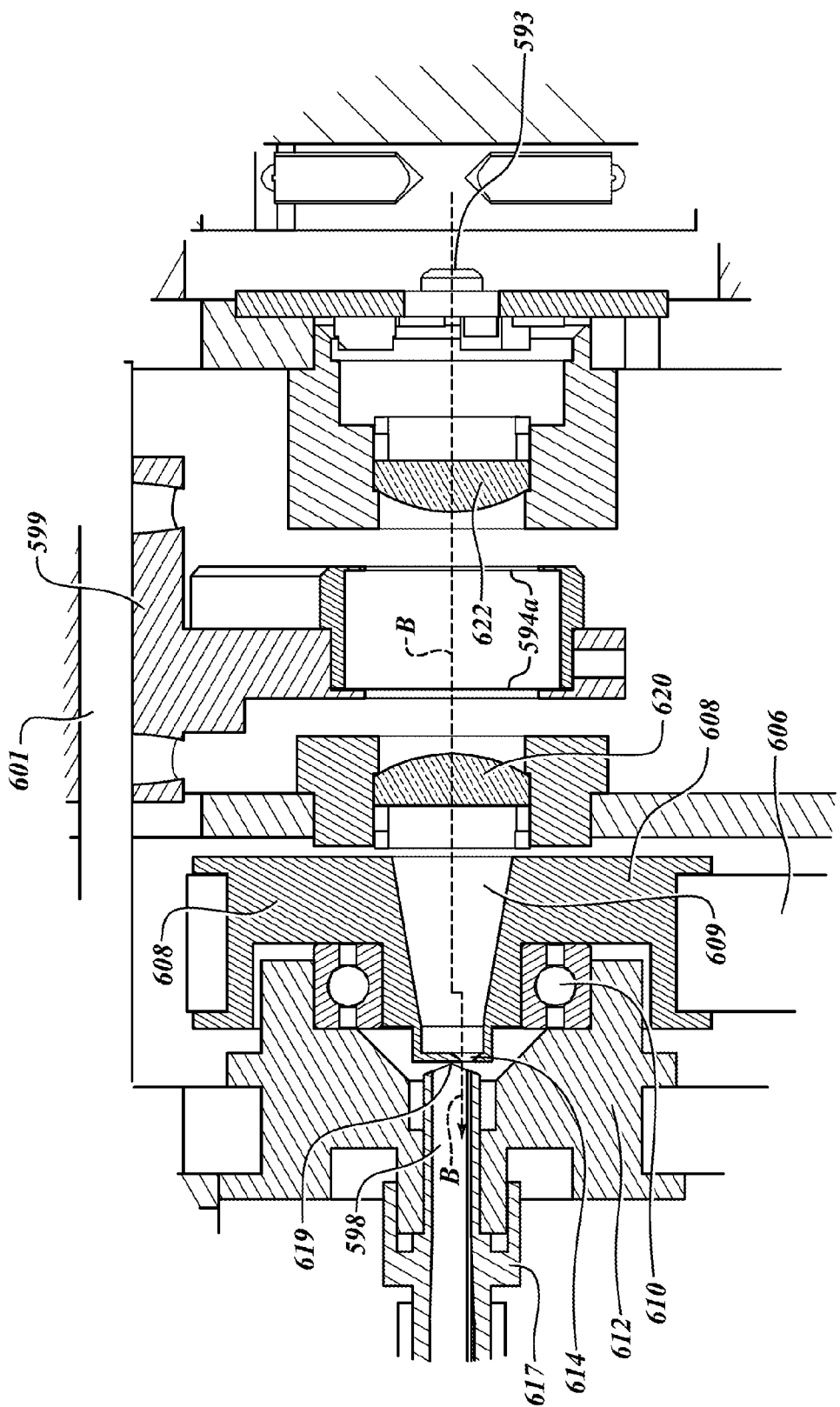
FIG. 26 is an enlarged view of a portion of the light source module shown on FIG. 25.

FIGS. 24-26 show the light source module 531 shown in FIG. 20. FIG. 24 shows a front view of the light source module 531; FIG. 25 shows a cross-sectioned view taken along lines 25-25 of FIG. 24; and FIG. 26 shows an enlarged view of a portion of FIG. 25. The light source module 531 includes a housing 591 having a filter selection device 592, a channel selection device 596, a light source 593, and a fiber housing device 595. In summary and with particular reference to FIGS. 25 and 26, the light source module 531 is configured to emit a light source to a single fiber of a fiber bundle 598, as depicted by energy path B for example, for illumination of a single specimen at a time. Energy path B is provided as a linear line for purposes of illustration. It should be appreciated that the light of the energy path may be focused and diverted by various components of the light source module 531, as further discussed herein.

The filter selection device 592 is configured to selectively position at least one filter 594 of a plurality of filters in the energy path B. The filter selection device 592 includes a filter wheel 599 with a plurality of pairs of filters 594 (2 pairs called out on FIGS. 24 and 25 as 594a, 594b). A first pair of filters 594a is shown on FIGS. 25 and 25 in a selected position in the energy path B. Alternatively, the pairs of the filters 594 may comprise a single filter. The filter selection device 592 further includes a filter selection motor 597 coupled to the filter wheel 599 via a shaft 601. The filter selection motor 597 is controlled to rotate the filter wheel 599 to position a selected pair of filters 594a in the energy path B.

The channel selection device 596 is configured to selectively allow the emission of light to a single optical fiber of the fiber bundle 598. The channel selection device 596 includes a channel selection wheel 600 and a motor 602 coupled to the channel selection wheel 600 via a shaft 604. The channel selection wheel 600 may be coupled to a gear 606 which may be coupled to an illumination wheel 608. Thus, the motor 602 is controlled to rotate the channel selection wheel 600, which rotates the gear 606, which rotates the illumination wheel 608. Both motors 597, 602 may be configured to rotate in either rotational direction.

The illumination wheel 608 may include an opening 609 positioned in the energy path B to capture the energy emitted by the light source 593. A bearing 610 is coupled to the illumination wheel 608 to allow free rotation of the illumination wheel 608. The bearing 610 is coupled to a support device 612 coupled to the housing 591; the support device 612 supports the illumination wheel 608 as it rotates. The illumination wheel 608 includes a channel selection aperture 614 to allow passage of light through the aperture 614 to one of the fibers of the fiber bundle 598. The channel selection aperture 614 may be formed off-center relative to a central longitudinal axis of the illumination wheel 608 so that, when the illumination wheel 608 is rotated, the position of the channel selection aperture 614 is changed radially so that the channel selection aperture 614 may allow passage of energy to a different fiber of the fiber bundle 598, as illustrated by energy path B shown on FIG. 26 extending through the channel selection aperture 614.

The fiber housing device 595 includes the fiber bundle 598 and is coupled to the support device 612. The fiber housing device 595 is configured to position the fiber bundle 598 adjacent the channel selection aperture 614 of the illumination wheel 608. The fiber housing device 595 includes a housing 616 and a connector 617 that connects the housing 616 to the support device 612. The housing 616 is coupled to the fiber line 533. The fiber line 533 includes the fiber bundle 598 having at least two fiber optic cables, which may be coupled to any illumination device for analysis of specimens. In the example shown on FIG. 20, the fiber line 533 is coupled to the illumination source mount 516.

The fiber bundle 598 extends through the housing 616 and into the connector 617. The connector 617 has an opening 619 positioned adjacent the channel selection aperture 614 of the illumination wheel 608. The fiber bundle 598 is positioned adjacent the opening 619, and consequently, adjacent the channel selection aperture 614. The fibers of the fiber bundle 598 may be arranged in a particular configuration, such as in a predetermined circular fashion. Accordingly, the illumination wheel 608 may be rotated to a selected position in order to position the channel selection aperture 614 adjacent a selected single optical fiber of the fiber bundle 598 such that light is transmitted to the single optical fiber for illumination of a particular specimen to be scanned.

A reference fiber 615 may be positioned adjacent the fiber bundle 598 for light fluctuation compensation while the light is illuminated from the light source to a selected single optical fiber. Because light sources tend to fluctuate during power supply, the reference channel is configured to transmit the light directly from the light source to a spectrophotometer sensor for a more accurate reading. In addition, sensors may be coupled to the components of the light source module 531 for a computer system to determine the position of a particular filter and a particular optical fiber relative to the energy path and relative to a particular specimen.

Once the specimen is scanned, the illumination wheel 608 may be rotated to a different position such that the channel selection aperture 614 is positioned adjacent a different single optical fiber of the fiber bundle for illumination of a specimen. Concurrently, the filter selection device 592 may be rotated between illuminations of specimens to position a particular filter in the energy path B, and the particular filter may be selected to correspond to the particular light source and the particular specimen to be illuminated. In the example shown on FIGS. 25 and 26, the pair of filters 594a includes a neutral density filter and a color filter. The other pairs of filters in the filter wheel 599 may be other types or combinations of filters.

The light source 593 may be an ultraviolet light source illuminated by 3 super bright white LEDs and 3 infrared LEDs to combine into a wavelength range of 200-1000 nm range of broad spectrum light, for example. A first lens 620 and a second lens 622 may each be positioned on either side of the filters 594a and in the energy path B. The lens 622 is configured to convert the light illuminated by the light source into parallel light so that the light can travel the distance from the lens 622 through the filters 594a in order to control the light intensity level and the particular wavelength of the light illuminated through the filters. The lens 622 may have a convex surface facing the filters 594a to spread the light as it passes through the filters 594a, and the lens 620 may have a convex surface facing the filters 594a on the other side of the filters to focus the parallel light into the opening 609 of the illumination wheel 608 and ultimately to a selected optical fiber of the fiber bundle 598 via the channel selection aperture 614.

CONCLUSIONS

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via microprocessors, Application Specific Integrated Circuits (ASICs), programmable logic controllers (PLCs), or programmable gate arrays (PGAs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers), as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Various methods and/or algorithms have been described. Some or all of those methods and/or algorithms may omit some of the described acts or steps, include additional acts or steps, combine acts or steps, and/or may perform some acts or steps in a different order than described. Some of the method or algorithms may be implemented in software routines. Some of the software routines may be called from other software routines. Software routines may execute sequentially or concurrently, and may employ a multi-threaded approach.

In addition, those skilled in the art will appreciate that the mechanisms taught herein are capable of being distributed as a program product in a variety of forms, and that an illustrative embodiment applies equally regardless of the particular type of nontransitory signal bearing media used to actually carry out the distribution. Examples of nontransitory signal bearing media include, but are not limited to, the following: recordable type media such as portable disks and memory, hard disk drives, CD/DVD ROMs, digital tape, computer memory, and other non-transitory computer-readable storage media.

The various embodiments described above can be combined to provide further embodiments.

Furthermore, the skilled artisan will recognize the interchangeability of various features from different embodiments disclosed herein. Similarly, the various features and acts discussed above, as well as other known equivalents for each such feature or act, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, it is not intended that the invention be limited, except as by the appended claims.

The various embodiments described above can be combined to provide further embodiments. All of the commonly assigned US patent application publications, US patent applications, foreign patents, foreign patent applications and non-patent publications referred to in this specification and/or listed in the Application Data Sheet, including but not limited to U.S. patent application Ser. No. 13/782,950, filed Mar. 1, 2013, are incorporated herein by reference, in their entirety.

What is claimed is:

1. A multi-channel analytical instrument, comprising:
   at least one illumination source operable to emit electromagnetic energy through a plurality of wells of a specimen receiver;
   a plurality of first ball lenses, each of the first ball lenses positioned proximate a respective one of a plurality of positions disposed on a first side of the specimen receiver and spaced from one another along a first dimension of the specimen receiver;
   a plurality of optical fibers that optically couple the at least one illumination source to respective ones of the first ball lenses;
   at least one sensor disposed on a second side of the specimen receiver, the at least one sensor responsive to electromagnetic energy received from the plurality of wells to produce a signal indicative of at least one characteristic of the electromagnetic energy; and a plurality of second ball lenses each positioned proximate a respective one of a plurality of positions disposed on the second side of the specimen receiver and spaced from one another along the first dimension of the specimen receiver, each of the second ball lenses which provides a respective optical path between a respective one of the wells and the at least one sensor.

2. The multi-channel analytical instrument of claim 1 wherein the second ball lenses are each optically coupled to the at least one sensor without any intervening optical fibers.

3. The multi-channel analytical instrument of claim 1, further comprising:
a plurality of sensor channels each disposed between a respective one of the second ball lenses and the at least one sensor.

4. The multi-channel analytical instrument of claim 1, further comprising:
a plurality of illumination channels each respectively disposed between a respective one of the optical fibers and a respective one of the first ball lenses.

5. The multi-channel analytical instrument of claim 1, further comprising:
a carriage that supports the plurality of optical fibers and the plurality of first and the plurality second ball lenses, the carriage operable to traverse the plurality of optical fibers along a plurality of columns of the wells of the specimen receiver.

6. The multi-channel analytical instrument of claim 5 wherein the carriage is slidably coupled to a guide member, whereby the carriage is movable in at least one direction relative to the specimen receiver.

7. The multi-channel analytical instrument of claim 5 wherein the carriage is slidably coupled to a guide member, whereby the carriage is movable in at least one direction relative to the specimen receiver.

8. The multi-channel analytical instrument of claim 1 wherein the at least one sensor includes a first sensor and a second sensor, the first sensor operable to capture an image of a specimen in the specimen receiver and the second sensor operable to scan the specimen in the specimen receiver.

9. The multi-channel analytical instrument of claim 1, further comprising:
a linear sensor array having a linear dimension and responsive to electromagnetic energy passed through at least one of the plurality of wells to produce a signal indicative of at least one characteristic of the passed-through electromagnetic energy.

10. The multi-channel analytical instrument of claim 9 wherein the linear sensor array is a global shutter sensor responsive to a control signal to concurrently sample pixels across the entire linear dimension of the linear sensor array.

11. The multi-channel analytical instrument of claim 1 wherein the plurality of optical fibers are configured to emit electromagnetic energy to a first row of wells at a first position of a plurality of positions, and further configured to move to a second position of the plurality of positions to emit electromagnetic energy to a second row of wells.

12. A multi-channel analytical instrument, comprising:
at least one illumination source operable to emit electromagnetic energy;
a receiver that has a plurality of wells to receive a sample, the receiver having at least a first dimension along which samples are spaced in the plurality of wells;
a first number of optical fibers coupled to the at least one illumination source;
a plurality of first ball lenses each positioned at a respective one of a plurality of positions disposed on a first side of the plurality of wells and spaced from one another along the first dimension of the receiver;
a plurality of second ball lenses each positioned at a respective one of a plurality of positions disposed on a second side of the plurality of wells and spaced from one another along the first dimension of the receiver; and
a linear sensor array, the linear sensor array responsive to electromagnetic energy received from the first number of optical fibers by the second plurality of ball lenses to produce a signal indicative of at least one characteristic of the electromagnetic energy.

13. The multi-channel analytical instrument of claim 12 wherein the linear sensor array is a global shutter sensor responsive to a control signal to concurrently sample pixels across the entire linear dimension of the linear sensor array.

14. The multi-channel analytical instrument of claim 12 wherein at least one of the plurality of first ball lenses is in an optical path between a respective first optical fiber and at least one of the plurality of second ball lenses, and at least one well of the plurality of wells is in the optical path positioned between the at least one of the plurality of first ball lenses and the at least one of the plurality of second ball lenses.

15. The multi-channel analytical instrument of claim 12 wherein the receiver includes a plurality of dimensions along which the first number of optical fibers are movable to emit electromagnetic energy through a plurality of wells along each of the plurality of dimensions.

16. The multi-channel analytical instrument of claim 12 wherein the plurality of second ball lenses are movable with the first number of optical fibers along the receiver to receive the electromagnetic energy from the first number of optical fibers.

17. The apparatus of claim 12, further comprising:
a plurality of illumination channels each disposed between a respective optical fiber of the first number of optical fibers and a respective ball lens of the plurality of first ball lenses.

18. The multi-channel analytical instrument of claim 12 wherein the second ball lenses are each optically coupled to the at least one sensor without any intervening optical fibers.

19. The apparatus of claim 12, further comprising:
a plurality of sensor channels each disposed between a respective second ball lens of the second ball lenses and the linear sensor array.

20. The apparatus of claim 12, further comprising:
a carriage supporting the first number of optical fibers, the plurality of first ball lenses, and the plurality of second ball lenses, the carriage movable in at least one direction relative to the receiver.

21. The multi-channel analytical instrument of claim 20 wherein the carriage is slidably coupled to a guide member, whereby the carriage is movable in the at least one direction relative to the receiver.

22. The multi-channel analytical instrument of claim 12 wherein the first number of optical fibers includes at least eight optical fibers, the at least eight optical fibers movable along an axis relative to the receiver.

23. A multi-channel analytical instrument, comprising:
at least one illumination source operable to emit electromagnetic energy;
at least one sensor, the at least one sensor responsive to electromagnetic energy to produce a signal indicative of at least one characteristic of the electromagnetic energy;
a plurality of first ball lenses, each of the first ball lenses positioned on a first side of a specimen receiver proximate a respective one of a plurality of positions spaced from one another along a first dimension of the specimen receiver;

a plurality of optical fibers that provide respective optically propogation paths between the at least one illumination source and respective ones of the first ball lenses;

a plurality of second ball lenses, each of the second ball lenses positioned on a second side of the specimen receiver proximate a respective one of the plurality of positions spaced from one another along the first dimension of the specimen receiver to align with respective ones of the first ball lenses, for each of the second ball lenses a respective optical path extends between the respective second ball lens and a respective position along the at least one sensor that passes through a respective one of the positions spaced from one another along the first dimension of the specimen receiver.

24. The multi-channel analytical instrument of claim 23 wherein the second ball lenses are each optically coupled to the at least one sensor without any intervening optical fibers.

25. The multi-channel analytical instrument of claim 23 wherein the specimen receiver includes a plurality of wells, and the respective optical path for each of the second ball lenses extends between the respective second ball lens through a respective one of the wells and to the at least one sensor.

26. The multi-channel analytical instrument of claim 25 wherein there are no optical fibers intervening between the second ball lenses and the at least one sensor.

\* \* \* \* \*